United States Patent
Wilson et al.

(10) Patent No.: US 12,102,732 B2
(45) Date of Patent: Oct. 1, 2024

(54) ORTHOPAEDIC IMPLANT

(71) Applicant: Smith & Nephew, Inc., Memphis, TN (US)

(72) Inventors: Darren Wilson, York (GB); John Rose, Collierville, TN (US); Nathaniel Kelley Grusin, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 12 days.

(21) Appl. No.: 17/405,446

(22) Filed: Aug. 18, 2021

(65) Prior Publication Data

US 2021/0386908 A1  Dec. 16, 2021

Related U.S. Application Data

(63) Continuation of application No. 16/064,352, filed as application No. PCT/US2017/014894 on Jan. 25, 2017.

(60) Provisional application No. 62/286,712, filed on Jan. 25, 2016.

(51) Int. Cl.
| | |
|---|---|
| A61L 27/34 | (2006.01) |
| A61L 27/06 | (2006.01) |
| A61L 27/54 | (2006.01) |
| B05D 1/18 | (2006.01) |
| B05D 3/10 | (2006.01) |
| B05D 7/14 | (2006.01) |

(52) U.S. Cl.
CPC ............. *A61L 27/34* (2013.01); *A61L 27/06* (2013.01); *A61L 27/54* (2013.01); *B05D 1/18* (2013.01); *B05D 3/108* (2013.01); *B05D 7/14* (2013.01); *A61L 2300/104* (2013.01); *A61L 2400/12* (2013.01); *A61L 2420/02* (2013.01); *B05D 2202/35* (2013.01)

(58) Field of Classification Search
CPC .......... A61L 27/34; A61L 27/06; A61L 27/30; A61P 11/00
See application file for complete search history.

(56) References Cited

U.S. PATENT DOCUMENTS

| | | |
|---|---|---|
| 5,326,567 A | 7/1994 | Capelli |
| 5,989,463 A | 11/1999 | Tracy et al. |
| 7,238,363 B2 | 7/2007 | Mansouri et al. |

(Continued)

FOREIGN PATENT DOCUMENTS

| | | |
|---|---|---|
| WO | 2005/087982 A1 | 9/2005 |
| WO | 2008/081861 A1 | 7/2008 |
| WO | 2009/111300 A2 | 9/2009 |

OTHER PUBLICATIONS

De Viteri et al., Titanium and Titanium Alloys as Biomaterials, 2013, Tribology-Fundamentals and Advancements, pp. 153-182 (Year: 2013).*

(Continued)

*Primary Examiner* — Dah-Wei D. Yuan
*Assistant Examiner* — Andrew J Bowman
(74) *Attorney, Agent, or Firm* — KDW Firm PLLC

(57) ABSTRACT

An orthopaedic implant comprising a titanium substrate having silver deposited thereon, wherein the silver is operable to be eluted at a rate of at least 0.25 µg/cm2 24 h−1, for at least 14 consecutive days, in use. The invention also extends to a method of producing an orthopaedic implant and use of the same.

18 Claims, 18 Drawing Sheets

(56) References Cited

U.S. PATENT DOCUMENTS

| | | | |
|---|---|---|---|
| 9,011,965 B2* | 4/2015 | Gan | A61P 19/00 |
| | | | 427/2.27 |
| 2012/0024712 A1 | 2/2012 | Neumann et al. | |
| 2013/0039953 A1* | 2/2013 | Dudnyk | A61P 11/00 |
| | | | 424/641 |

OTHER PUBLICATIONS

Ewald et al., Antimicrobial titanium/silver PVD coatings on titanium, 2006, Biomedical Engineering Online, vol. 5, No. 22, pp. 1-20 (Year: 2006).*

Search Report for European Patent Application No. 17704606.7, mailed Dec. 19, 2019.

Flores, C. Y., et al., "Citrate-Capped Silver Nanoparticles Showing Good Bactericidal Effect against Both Planktonic and Sessile Bacteria and a Low Cytotoxicity to Osteoblastic Cells", ACS Applied Materials & Interfaces, 5(8):3149-3159, Apr. 24, 2013.

Harada, R., et al., "Influence of sulfide concentration on the corrosion behavior of titanium in a simulated oral environment", Materials Science and Engineering C, 62:268-273 Jan. 26, 2016.

Hardes, J., et al. "Reduction of Periprosthetic Infection With Silver-Coated Megaprostheses in Patients With Bone Sarcoma", Journal of Surgical Oncology, 101:389-395, Jan. 1, 2010.

International Search Report and Written Opinion for International Application No. PCT/US2017/014894, mailed Jul. 27, 2017.

* cited by examiner

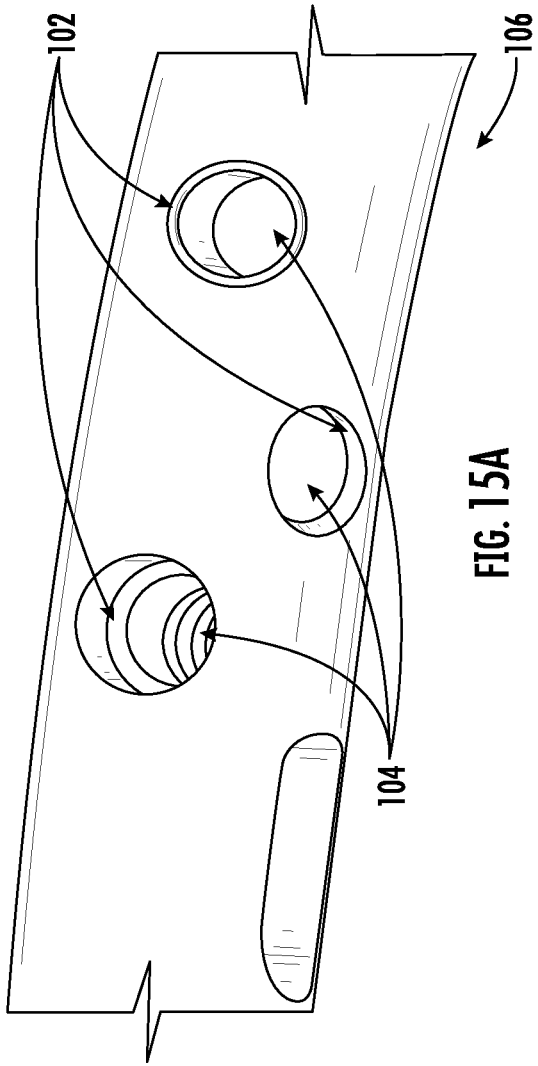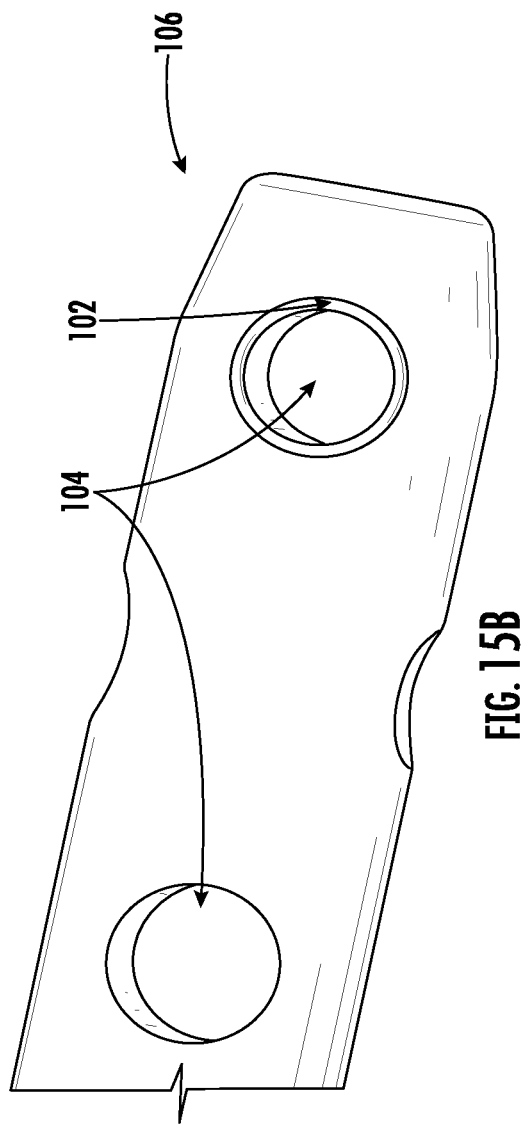

ORTHOPAEDIC IMPLANT

CROSS-REFERENCE TO RELATED APPLICATIONS

This application is a continuation application of U.S. patent application Ser. No. 16/064,352, filed Jun. 20, 2018, which is a U.S. National Phase of International PCT Application No. PCT/US2017/014894, filed on Jan. 25, 2017, which claims the benefit of U.S. Provisional Patent Application No. 62/286,712, filed on Jan. 25, 2016, the contents of each application are hereby incorporated by reference herein in their entirety.

FIELD OF THE DISCLOSURE

The present invention relates to orthopaedic implants, methods of producing the same and uses thereof. In particular to orthopaedic implants having antimicrobial properties, methods of producing the same and uses thereof are provided.

BACKGROUND OF THE DISCLOSURE

Tens of millions of medical devices are used each year. Despite advances in biomaterials, bacteria colonize a significant proportion of these devices, which becomes the focus of an implant-related infection. Studies have been performed indicating that a minimum of about 10,000 bacteria are required to cause an infection in non-implant situations, whereas as few as ten (10) can cause an infection in the presence of an implant coated in serum proteins. In the case of infections affecting joint prostheses, the probability of a cure without removal of the implant is low, so the usual treatment is removal of the infected component.

In order to address this shortcoming, a wide spectrum of substances and technological approaches has been proposed and tested for creating antibacterial surfaces. This approach assumes that non-adherent bacteria can be efficiently eradicated either by the immune system or systemic antibiotics.

In particular, silver is the most prevalent metal used in biomedical applications given its history of use as a proven broad-spectrum antimicrobial agent in either an ionic or nano-crystalline format. It also offers a lower risk for generating antimicrobial resistant strains than conventional antibiotics, which is a serious and growing global threat to public health.

When looking at metal medical devices such as an orthopaedic implant, there are a number of techniques available for incorporating silver into the surface of a metal. For example, in a titanium device, the creation of a silver titanate reservoir using chemical passivation provides a low-cost option for mass producing titanium implants with antimicrobial properties. However, the elution profile of the silver is limited to a maximum of one week, with a large portion of the silver eluted within the first few days with a waning elution rate thereafter. This makes it less effective as a treatment option for patients sustaining open fractures given that the amount of silver being eluted is typically under the minimum inhibitory concentration (MIC) in the course of anti-infective treatment.

A sustained-release formulation (i.e., regulating the silver release rate in a controlled matter) would be required to overcome the relatively short half-life of silver, the high bioavailability to biological molecules (serum proteins), and incidence of forming silver chlorides with low solubility. Therefore, to maintain effective antimicrobial activity, a sustained-release formulation would be required.

Furthermore, even if a sustained-release formulation could be achieved, it has hitherto not been possible to achieve high enough silver loading in a titanium orthopaedic device such that sustained elution, if achievable, would elute more than the minimum inhibitory concentration (MIC) silver continuously over a sustained period such as, for example, consistently for more than one week.

Other potential drawbacks to commercializing silver titanate treated devices are the uncontrolled colour changes after processing leading to the device turning black. This can be particularly problematic because it is necessary to identify the device upon insertion, which is usually achieved by laser marking or a removable tab.

It is an aim of certain aspects of the present invention to address the above-mentioned items and/or other problems.

SUMMARY OF THE DISCLOSURE

According to a first aspect of the present invention, there is provided an orthopaedic implant comprising a titanium substrate having silver deposited thereon, wherein the silver is operable to be eluted at a rate of at least 0.25 $\mu g/cm^2$ 24 $h^{-1}$, for at least 14 consecutive days, in use.

Suitably, the silver may be operable to be eluted at a rate of at least 0.5 $\mu g/cm^2$ 24 $h^{-1}$, for at least 14 consecutive days, in use; such as at least 0.75 $\mu g/cm^2$ 24 $h^{-1}$, for at least 14 consecutive days, in use; or at least 1 $\mu g/cm^2$ 24 $h^{-1}$, for at least 14 consecutive days, in use.

Suitably, the silver may be operable to be eluted at a rate of at least 0.25 $\mu g/cm^2$ 24 $h^{-1}$, for at least 21 consecutive days, in use; such as at least 0.25 $\mu g/cm^2$ 24 $h^{-1}$, for at least 28 consecutive days, in use; or at least 0.25 $\mu g/cm^2$ 24 $h^{-1}$, for at least 35 consecutive days, in use.

Suitably, the silver may be operable to be eluted at a rate of at least 0.5 $\mu g/cm^2$ 24 $h^{-1}$, for at least 21 consecutive days, in use; such as at least 0.5 $\mu g/cm^2$ 24 $h^{-1}$, for at least 28 consecutive days, in use; or at least 0.5 $\mu g/cm^2$ 24 $h^{-1}$, for at least 35 consecutive days, in use.

Suitably, the silver may be operable to be eluted at a rate of at least 0.75 $\mu g/cm^2$ 24 $h^{-1}$, for at least 21 consecutive days, in use; such as at least 0.75 $\mu g/cm^2$ 24 $h^{-1}$, for at least 28 consecutive days, in use; or at least 0.75 $\mu g/cm^2$ 24 $h^{-1}$, for at least 35 consecutive days, in use.

Suitably, the silver may be operable to be eluted at a rate of at least 1 $\mu g/cm^2$ 24 $h^{-1}$, for at least 21 consecutive days, in use; such as at least 1 $\mu g/cm^2$ 24 $h^{-1}$, for at least 28 consecutive days, in use; or at least 1 $\mu g/cm^2$ 24 $h^{-1}$, for at least 35 consecutive days, in use.

Reference(s) herein to a titanium substrate having silver deposited "thereon" refers to deposition on or within the substrate surface region, which may be the top surface layer(s) and/or layer(s) near to the top surface layer(s).

The silver deposited on the titanium substrate suitably comprises silver ions and/or silver nanoparticles. The silver ions and/or silver nanoparticles may be dispersed either within or on top of a titanate nanostructure.

Reference(s) herein to "in use" refers to use of the orthopaedic implant in the physiological environment (i.e., in situ).

In one embodiment, the orthopaedic implant may further comprise a polymeric coating.

Therefore, according to a further aspect of the present invention, there is provided an orthopaedic implant comprising a titanium substrate having silver deposited thereon, and being coated with a polymeric coating, wherein the silver is operable to be eluted at a rate of at least 0.25 µg/cm² 24 h⁻¹, for at least 14 consecutive days, in use.

Advantageously, adding a polymeric coating enables a controlled release of the silver from the implant into the body. This allows for a beneficial sustained controlled release of the silver and also reduces the cytotoxicity of large amounts of silver being released into the body.

According to a further aspect of the present invention, there is provided a method of forming an orthopaedic implant comprising applying a polymeric coating to a titanium substrate having silver deposited thereon.

According to a further aspect of the present invention, there is provided a method of controlling the elution of silver from an orthopaedic implant, the orthopaedic implant comprising a titanium substrate having silver deposited thereon, the method comprising applying a polymeric coating to the titanium substrate having silver deposited thereon.

According to a further aspect of the present invention, there is provided the use of a polymeric coating for controlling the elution of silver from an orthopaedic implant, the orthopaedic implant comprising a titanium substrate having silver deposited thereon.

Suitably, the polymeric coating is biocompatible. For the avoidance of doubt, the term "biocompatible" means a polymeric coating that is not, for example, harmful or toxic to living tissue.

Suitably, the polymeric coating comprises a polymer material. The polymeric coating may comprise any suitable polymer material. Suitably, the polymer material may be biodegradable. For the avoidance of doubt, the term "biodegradable" means a material that may be hydrolysed or degraded by enzymes in the physiological environment (i.e., in situ) and subsequently absorbed or metabolised.

In certain embodiments, the polymer material may comprise a natural polymer, a synthetic polymer, or a combination thereof.

Examples of suitable natural polymers include, but are not limited to, one or more of the following: hemaleucin; gelatin; starch; cellulose; chitosan; collagen; or combinations thereof. Suitably, the polymeric material may comprise hemaleucin, gelatin or a combination thereof.

Examples of suitable synthetic polymers include, but are not limited to, one or more of the following: polyesters such as, for example, polylactides (including poly-D-lactides, poly-L-lactides, poly-D,L-lactides and combinations thereof), polyglycolides, polylactide-polyglycolide copolymers (including poly-D-lactide-polyglycolide copolymers, poly-L-lactide-polyglycolide copolymers, poly-D,L-lactide-polyglycolide copolymers and combinations thereof) and polyester-polyethylene glycol (PEG) copolymers; poly-orthoesters; polyamino acids; polyurethanes; or combinations thereof. Suitably, the polymeric material may comprise poly-D, L-lactide-polyglycolide copolymers, poly-D, L-lactides or a combination thereof.

In certain embodiments, when the polymeric material may comprise a polylactide-polyglycolide copolymer, the molar ratio of lactide to glycolide may be from about 20:1 to 1:20, suitably from about 10:1 to 1:10, such as about 5:1 to 1:5, or even from 2:1 to 1:2. Suitably, when the polymeric material is a polylactide-polyglycolide copolymer, the molar ratio of lactide to glycolide may be about 1:1.

In certain embodiments, when the polymeric material may comprise a polylactide-polyglycolide copolymer, the molar ratio of lactide to glycolide may be about 1:1.

In certain embodiments, when the polymeric material may comprise a polylactide-polyglycolide copolymer, the molar ratio of lactide to glycolide may be about 3:1.

In certain embodiments, the polymer material may comprise a commercially available polymer material. Examples of suitable commercially available polymer materials include, but are not limited to, those sold under the trade name PURASORB such as, for example, PURASORB PDLG 5010, PURASORB PDLG 7507, PURASORB PDL 02A, PURASORB PDL 02, PURASORB PDL 04, PURASORB PDL 20 and PURASORB PDL 45 (available from Corbion).

The polymer material may have any suitable weight-average molecular weight (Mw). In certain embodiments, the polymer material may have an Mw from about 1,000 to 1,000,000 Daltons (Da=g/mole), suitably from about 5,000 to 1,000,000 Da, such as from about 10,000 to 1,000,000 Da, or even from about 10,000 to 900,000 Da.

The weight-average molecular weight may be measured by any suitable method. Techniques to measure the weight-average molecular weight will be well known to a person skilled in the art. Suitably, the Mw may be determined by gel permeation chromatography using a polystyrene standard.

The polymer material may have any suitable inherent viscosity. In certain embodiments, the polymer material may have an inherent viscosity from about 0 to 10 dl/g, suitably from about 0 to 7 dl/g, such as from about 0.01 to 7 dl/g, or even from about 0.01 to 5 dl/g.

The inherent viscosity may be measured by any suitable method. It will be well known to a person skilled in the art that inherent viscosity is based on the flow time of a polymer solution through a narrow capillary relative to the flow time of the pure solvent through the capillary. Suitable methods will be well known to a person skilled in the art. Suitably, the inherent viscosity may be measured using $CHCl_3$ as solvent at 25° C. and at a concentration of 0.1 g/dl.

The orthopaedic implant is coated with the polymeric coating. The terms "coated," "being coated" or like terms, as used herein, means that that the polymeric coating is applied to at least a portion of orthopaedic implant.

The polymeric coating may be applied to the orthopaedic implant by any suitable method. Methods of applying the polymeric coating will be well known to a person skilled in the art. Examples of suitable application methods include, but are not limited to, one or more of the following: spray coating; roll coating; dip coating; electro coating; or combinations thereof. Suitably, the polymeric coating may be applied to the orthopaedic implant by dip coating.

Advantageously, applying the polymeric coating to the orthopaedic implant by dip coating provides a more uniform coverage of the exposed surfaces thereof. This is particularly the case where the orthopaedic implant is cannulated, and therefore has a very narrow internal passage.

Dip coating methods are well known to a person skilled in the art. Typically, dip coating methods comprise the following steps: (i) immersing a substrate in a coating solution comprising a polymeric material and a solvent, (ii) withdrawing the substrate from the coating solution to form a wet layer, and (iii) curing the coating by solvent evaporation. Accordingly, the polymeric coating of the present invention may be applied to the orthopaedic implant by dip coating, the dip coating comprising the steps of: (i) immersing the orthopaedic substrate in a coating solution comprising the polymeric material and a solvent, (ii) withdrawing the orthopaedic substrate from the coating solution to form a wet layer, and (iii) curing the polymeric coating.

The coating solution may comprise any suitable solvent. The solvent may comprise a single solvent or a mixture of solvents. The solvent may comprise water, an organic solvent or a mixture of water and organic solvent. Examples of suitable solvents include, but are not limited to, one or more of the following: tetrahydrofuran (THF); dichloromethane; chloroform; ethyl acetate; propyl acetate; ethyl propionate; isopropyl acetate; isoamyl acetate; propylene glycol monomethyl ether acetate; dimethyl carbonate; methylene chloride; anisole; cyclopentanone; cyclohexanone; hexafluoro-2-propanol (HFIP); acetone; N-methyl-2-pyrrolidone (NMP); supercritical fluids such as supercritical $CO_2$ and supercritical HFC-134a; and combinations thereof. In certain embodiments, the solvent may comprise tetrahydrofuran (THF); chloroform; ethyl acetate; hexafluoro-2-propanol (HFIP); acetone; N-methyl-2-pyrrolidone (NMP); dimethyl carbonate; and combinations thereof. Suitably, the solvent may comprise ethyl acetate, dimethyl carbonate, or combinations thereof.

In certain embodiments, the solvent may comprise ethyl acetate.

In certain embodiments, the solvent may comprise dimethyl carbonate.

It will be appreciated by a person skilled in the art that the solvent should be selected such that the polymeric material may be substantially fully dissolved in the selected solvent.

The polymeric material may be present in the coating solution at any suitable concentration. In certain embodiments, the polymeric material may be present in the coating solution at a concentration of about 2.5 to 50% weight/volume (w/v), suitably about 2.5 to 30% w/v, such as about 5 to 30% w/v, or even from about 5 to 20% w/v. For the avoidance of doubt, the terms "weight/volume," "w/v" or like terms, as used herein, refers to the weight in grams (g) of the polymeric material over the volume of the solvent in millilitres (ml).

It will be appreciated by a person skilled in the art that the orthopaedic implant may be partially immersed or may be fully immersed in the coating solution in step (i).

The polymeric coating may be applied to the orthopaedic implant by dip coating at any suitable rate. In certain embodiments, the polymeric coating may be applied to the orthopaedic implant at a rate of about 20 to 500 mm/min, suitably about 10 to 1000 mm/min, such as about 20 to 700 mm/min, or even about 30 to 500 mm/min. Suitably, the polymeric coating may be applied to the orthopaedic implant by dip coating at a rate of about 50 to 300 mm/min.

In certain embodiments, the polymeric coating may be applied to the orthopaedic implant by dip coating at a rate of about 50 mm/min.

Advantageously, applying the polymeric coating to the orthopaedic implant by dip coating at the above-mentioned rates results in an improved silver ion elution profile.

Curing the polymeric coating (i.e., in step (iii)) may be carried out by any suitable method. It will be appreciated by a person skilled in the art that the polymeric coating may be cured by solvent evaporation. In certain embodiments, the polymeric coating may be heat cured. Suitably, the polymeric coating may be cured at temperatures of about 30 to 100° C., such as about 40 to 60° C., or even about 50° C., for about 30 to 90 minutes, such as about 45 to 75 minutes, or even about 60 minutes.

The polymeric coating may be applied to the orthopaedic implant to any suitable dry film thickness. In certain embodiments, the polymeric coating may be applied to the orthopaedic implant to a dry film thickness of about 0.5 to 10 microns (μm), suitably about 0.5 to 5 μm, such as about 1 to 5 μm, or even about 1.5 to 4 μm. Suitably, the polymeric coating may be applied to the orthopaedic implant to a dry film thickness of about 2 to 3 microns (μm).

The polymeric coating may be applied to the orthopaedic substrate as a single layer or in multiple layers, such as, two, three or four layers.

The polymeric coating may also comprise a bioactive material, such as bioactive metal. In this manner, the polymeric coating may comprise, for example, silver.

The polymeric coating may also comprise one or more biofilm disrupting agents. The biofilm disrupting agent will tend to comprise one or more proteins operable to disrupt a biofilm. In this manner, antibiotic penetration may be increased.

Examples of biofilm disrupting agents that may be included in the polymeric coating or within the titanate reservoir include one or more of the following:

| Disruptor | Examples |
| --- | --- |
| Quorum Sensing | Furanones C-30 and C-56, RNAIII-inhibiting peptide (RIP), Acyl-homoserine lactones, gamma-butyrolactones, oligopeptides, and AI-2 molecules |
| Enzymes | Ethylenediaminetetraacetic acid (EDTA) glycosidases, proteases, deoxyribonucleases, alginate lyase and thermonuclease |
| Peptides/Proteins | LL-37, 1026, 1029, 1036, 1037 |
| General Disinfectant | Iodine, chlorite, and chlorohexidine's, Alexidine |
| Other Metal | Copper, zinc, mercury, chromium, manganese, nickel, cadmium, arsenic, cobalt, aluminum, lead, selenium, platinum, gold, titanium, tin, barium, vanadium, bismuth, iron, strontium, antimony |
| Antibiotic Based | Gentamycin, Vancomycin, tobramycin |
| Silver | Silver and associated derivatives/compositions |
| Detergents/Surfactants | Biosurfactants/bioemulsifiers that target the Exopolysaccharides (EPS), e.g., Surfactin, Rhamnolipids |
| Lactones | Lactones, furones |
| Amino Acids | N-Acetyl Cysteine |
| Polysaccharides | Thiolated chitosan's, alginates and charged polyamino acids |
| Amine/ide | Amines, Amides |
| Nanoparticles | Magnesium fluoride, NO-releasing nanoparticles, superparamagnetic iron oxide NPs (SPIONs), silver NPs |
| Peroxides | Hydrogen peroxide |
| Nitric Oxide/Nitrate | Gaseous nitric oxide |
| Antibody/Immune | TRL1068 |
| Encapsulation | Liposomal encapsulation of agents to penetrate biofilms |
| Biguanidines | Metformin |
| Sugars | Xylitol, D-tagatose |

-continued

| Disruptor | Examples |
|---|---|
| Triazole/ine | Imidazole derivatives-Triazole and Triazines |
| Salts | Siloxane quaternary ammonium salts, oxazolidionone |
| Phenols | Obtusastyrene (4-cinnamylphenol) |

According to a further aspect of the present invention, there is provided an orthopaedic implant comprising a titanium substrate having silver deposited thereon and having a polymeric coating thereon, the polymeric coating being applied to the titanium substrate having silver deposited thereon at a rate of between 10 mm/min and 1000 mm/min.

According to a further aspect of the present invention, there is provided an orthopaedic implant comprising a titanium substrate having silver deposited thereon and having a polymeric coating thereon, the polymeric coating being operable to allow elution of the silver into the body at a rate at least 0.25 µg/cm$^2$ 24 h$^{-1}$, in use, and being obtainable by applying the polymer coating to the titanium substrate having silver deposited thereon at a rate of between 10 mm/min and 1000 mm/min.

According to a further aspect of the present invention, there is provided a method of forming an orthopaedic implant comprising applying a polymeric coating to a titanium substrate having silver deposited thereon, wherein the polymeric coating is applied to the titanium substrate having silver deposited thereon at a rate of between 10 mm/min and 1000 mm/min.

Suitably, the polymer is deposited onto the titanium substrate having silver deposited thereon at a rate of between 30 mm/min and 500 mm/min, such as between 50 mm/min and 300 mm/min.

In one embodiment, it has been found that the elution rate can be altered by subjecting the orthopaedic implant to a heat treatment.

Therefore, according to a further aspect of the present invention, there is provided an orthopaedic implant comprising a titanium substrate having silver deposited thereon, wherein the silver is operable to be eluted at a rate of at least 0.25 µg/cm$^2$ 24 h$^{-1}$, for at least 14 consecutive days, in use, obtainable by subjecting the titanium substrate having silver deposited thereon to a heat treatment.

Suitably, the heat treatment may comprise exposing the titanium substrate having silver deposited thereon to an elevated temperature, such as, for example, a temperature of above 100° C., or above 150° C., such as above 200° C., or even above 250° C., for a time period T.

In one embodiment, the heat treatment may comprise exposing the titanium substrate having silver deposited thereon to temperature of between about 250° C. and 310° C., such as about 280° C., for a time period T.

The time period T may be at least 15 minutes, such as at least 30 minutes or at least 60 minutes. The time period T may be at least 90 minutes. The time period T may be between about 90 minutes and 150 minutes, such as about 120 minutes, for example.

It will be appreciated by one skilled in the art that the orthopaedic implant of the present invention may obtainable by both subjecting the titanium substrate having silver deposited thereon to a heat treatment and also have a polymeric coating applied thereto, if desired.

An implant has also been developed having a high loading of silver thereon.

According to a further aspect of the present invention, there is provided an orthopaedic implant comprising a titanium substrate having silver deposited thereon at an amount of at least 10 µg/cm$^2$.

Suitably, the orthopaedic implant may comprise a titanium substrate having silver deposited thereon at an amount of at least 20 µg/cm$^2$, such as at least 40 µg/cm$^2$, or at least 50 µg/cm$^2$, for example at least 75 µg/cm$^2$. In one embodiment, the orthopaedic implant may comprise a titanium substrate having silver deposited thereon at an amount of at least 100 m/cm$^2$.

The level of silver deposited on the titanium substrate can be determined using either destructive or non-destructive techniques. Destructive techniques include Inductively Coupled Plasma-Optical; Emission Spectroscopy (ICP-OES), Inductively Coupled Plasma-Mass Spectroscopy (ICP-MS), Flame or Furnace Atomic Absorption Spectrometry (AAS), UV-Vis spectroscopy with ICP-MS being the preferred method given its lower detection limits. Non-destructive techniques include X-ray fluorescence, Spectroscopy using a handheld gun whereby electrons are displaced from their atomic orbital positions, releasing a burst of energy that is characteristic of a specific element. If the bioactive agent(s) is a biological protein, quantification can be achieved using enzyme-linked immunosorbent assays (ELISA), flow cytometry or other suitable fluorescence-based and colorimetric assays.

Suitably, the level of silver deposited on the titanium substrate can be determined using Inductively Coupled Plasma-Mass Spectroscopy (ICP-MS) in accordance with ISO 10993:2005 Part 18 ("Chemical characterisation of materials"), wherein silver is first stripped from the titanium substrate using acid digestion and is subsequently subjected to analyses using Inductively Coupled Mass Spectroscopy (ICP MS). Typically, the titanium substrate is immersed in 10 ml of a 2:1 nitric acid:deionised water solution and left overnight. Then, these solutions are mixed by vortex and serially diluted 1,000× with a 1% solution of nitric acid. The diluted solutions are then analysed using ICP MS to quantify the silver content under the following conditions: instrument—Agilent 8800 ICP-MS triple quad; autosampler—ASX-500 series; sample introduction—peri pump; nebuliser—micro mist; lens type—x; scan—single quad; plasma mode—general purpose; acquisition mode—spectrum; spectrum mode options—Q2 peak patterns 3 pts, 3 reps, 100 sweeps/rep; elements—Rh (IS) (mass 103, int time 0.3 s), Ag (mass 107, int time 0.3 s).

In one embodiment, it has been established that subjecting the titanium substrate to an alkali passivation process prior to silver deposition, using a Group I or Group II metal hydroxide at between 7 and 13 M concentration, increases the level of silver deposition.

Therefore, according to a yet further aspect of the present invention, there is provided an orthopaedic implant comprising a titanium substrate having silver deposited thereon, wherein the titanium substrate having the silver deposited thereon is obtainable by contacting the titanium substrate with a 7 to 13M solution of a group I or group II metal hydroxide to thereby passivate the titanium substrate, then contacting the passivated titanium substrate so obtained with a silver material.

According to a further aspect of the present invention, there is provided a method of forming an orthopaedic implant comprising contacting a titanium substrate with a 7 to 13M solution of a group I or group II metal hydroxide to thereby passivate the titanium substrate, then contacting the passivated titanium substrate so obtained with a silver material.

The group I or group II metal hydroxide is selected from one or more of the following: lithium hydroxide, sodium hydroxide, potassium hydroxide, beryllium hydroxide, magnesium hydroxide or calcium hydroxide. In one embodiment, the group I or group II metal hydroxide comprises sodium hydroxide.

Suitably, the solution of a group I or group II metal hydroxide has a molarity of between 8M and 12M, such as between 9M and 11M. In one embodiment, the solution of a group I or group II metal hydroxide has a molarity of substantially 10M.

Suitably, the titanium substrate is contacted with the solution of a group I or group II metal hydroxide for a time period of at least 30 minutes, such as at least 1 hour, for example at least 2 hours. In one embodiment, the titanium substrate is contacted with the solution of a group I or group II metal hydroxide for a time period of at least 4 hours, such at least 6 hours, or even at least 7 hours.

Suitably the silver material comprises a silver salt. Suitably, the silver salt has a concentration of at least 0.01M, such as at least 0.02M or even at least 0.05M, such as at least 0.06M. Suitably, the silver salt has a concentration of between 0.05 and 0.15M, such as between 0.06M and 0.1M.

In one embodiment, the silver salt comprises silver nitrate.

It has also been found by the present inventors that the temperature at which the titanium substrate is contacted with the solution of a group I or group II metal hydroxide affects the silver loading of the orthopaedic implant.

In one embodiment, the titanium substrate is contacted with the solution of a group I or group II metal hydroxide at a temperature of at least about 65° C., such as at least 70° C., or even at least 75° C.

According to a further aspect of the present invention, there is provided an orthopaedic implant comprising a titanium substrate having silver deposited thereon and over coated with a polymeric coating, wherein the silver is operable to be eluted at a rate of at least 0.25 $\mu g/cm^2$ 24 $h^{-1}$, for at least 14 consecutive days, in use, and wherein the titanium substrate having the silver deposited thereon is obtainable by contacting the titanium substrate with a 7 to 13M solution of a group I or group II metal hydroxide to thereby passivate the titanium substrate, then contacting the passivated titanium substrate with a silver material.

Suitably the silver material comprises a silver salt, such as, for example, silver nitrate.

Previously, the use of silver on a titanium substrate has led to problems of blackening. It is necessary for orthopaedic implants to be visually identifiable for ease of use, but also to record the serial number of the implant in the patient. These serial numbers are often laser etched onto the orthopaedic implants. However, the use of silver on a titanium substrate leads to the orthopaedic implant having a black or blackened colour such that the laser etched serial number becomes illegible upon implantation.

However, certain aspects of the present invention have identified a way to mitigate the blackening of the device, and therefore alleviate the above-mentioned problem. In particular, the present invention has identified a number of agents that reduce blackening, referred to herein as blackening reducing agents.

Accordingly, the titanium substrate having silver deposited thereon of the orthopaedic device of the present invention may be contacted with a blackening reducing agent.

Therefore, according to a further aspect of the present invention, there is provided an orthopaedic implant comprising a titanium substrate having silver deposited thereon, wherein the titanium substrate having silver deposited thereon is contacted with a blackening reducing agent.

According to a further aspect of the present invention, there is provided a method of forming an orthopaedic implant, the orthopaedic implant comprising a titanium substrate having silver deposited thereon, the method comprising contacting the titanium substrate having silver deposited thereon with a blackening reducing agent.

According to a further aspect of the present invention, there is provided a method of reducing blackening in an orthopaedic implant, the orthopaedic implant comprising a titanium substrate having silver deposited thereon, the method comprising contacting the titanium substrate having silver deposited thereon with a blackening reducing agent.

The blackening reducing agent is suitably selected from one or more of the following: polyvinylpyrrolidone, poly (vinyl alcohol), poly(ethylene glycol), sodium chloride, sodium sulphide, alkaline glucose, sodium citrate, ascorbate, poly (ethylene glycol)-block, and sodium borohydride.

In one embodiment, the blackening reducing agent comprises sodium sulphide.

According to a further aspect of the present invention, there is provided a method of reducing blackening in an orthopaedic implant, the orthopaedic implant comprising a titanium substrate having silver deposited thereon, the method comprising contacting the titanium substrate having silver deposited thereon with sodium sulphide.

According to a further aspect of the present invention, there is provided the use of sodium sulphide for reducing the blackening of an orthopaedic implant, the orthopaedic implant comprising a titanium substrate having silver deposited thereon, the use comprising contacting the titanium substrate having silver deposited thereon with sodium sulphide.

It has advantageously been found in the present invention that the use of sodium sulphide as a blackening reducing agent also retains a high level of silver in the orthopaedic device.

Therefore, according to a further aspect of the present invention, there is provided an orthopaedic implant comprising a titanium substrate having silver deposited thereon, wherein the titanium substrate having silver deposited thereon is contacted with a blackening reducing agent, such as sodium sulphide, and wherein the silver is operable to be eluted at a rate of at least 0.25 $\mu g/cm^2$ 24 $h^{-1}$, for at least 14 consecutive days, in use.

It should be appreciated that although the previous statements refer to silver, any bioactive metal ion could be deposited onto the titanium substrate.

Suitably, the bioactive metal is selected from one or more of the following: silver, gold, copper, tin, antimony, platinum, gallium, palladium, and zinc.

The bioactive metal deposited on the titanium substrate suitably comprises bioactive metal ions and/or bioactive metal nanoparticles.

According to a further aspect of the present invention there is provided an orthopaedic implant comprising a titanium substrate having bioactive metal deposited thereon, wherein the bioactive metal is operable to be eluted at a rate of at least 0.25 µg/cm$^2$ 24 h$^{-1}$, for at least 14 consecutive days, in use.

According to a further aspect of the present invention, there is provided an orthopaedic implant comprising a titanium substrate having bioactive metal deposited thereon, and being coated with a polymeric coating, wherein the bioactive metal is operable to be eluted at a rate of at least 0.25 µg/cm$^2$ 24 h$^{-1}$, for at least 14 consecutive days, in use.

According to a further aspect of the present invention, there is provided an orthopaedic implant comprising a titanium substrate having bioactive metal deposited thereon and having a polymer coating thereon, the polymer coating being applied to the titanium substrate having bioactive metal deposited thereon at a rate of between 10 mm/min and 1000 mm/min.

According to a further aspect of the present invention there is provided an orthopaedic implant comprising a titanium substrate having bioactive metal deposited thereon and having a polymer coating thereon, the polymer coating being operable to allow elution of the bioactive metal into the body at a rate at least 0.25 µg/cm$^2$ 24 h$^{-1}$, in use, and being obtainable by applying the polymer coating to the titanium substrate having bioactive metal deposited thereon at a rate of between 10 mm/min and 1000 mm/min.

According to a further aspect of the present invention, there is provided an orthopaedic implant comprising a titanium substrate having bioactive metal deposited thereon, wherein the bioactive metal is operable to be eluted at a rate of at least 0.25 µg/cm$^2$ 24 h$^{-1}$, for at least 14 consecutive days, in use, obtainable by subjecting the titanium substrate having bioactive metal deposited thereon to a heat treatment.

According to a further aspect of the present invention, there is provided an orthopaedic implant comprising a titanium substrate having bioactive metal deposited thereon at an amount of at least 10 µg/cm$^2$.

According to a further aspect of the present invention, there is provided an orthopaedic implant comprising a titanium substrate having bioactive metal deposited thereon wherein the titanium substrate having the bioactive metal deposited thereon is obtainable by contacting the titanium substrate with a 7 to 13M solution of a group I or group II metal hydroxide, and then contacting the passivated titanium substrate so obtained with a bioactive metal material.

According to a further aspect of the present invention, there is provided an orthopaedic implant comprising a titanium substrate having bioactive metal deposited thereon and over coated with a polymeric coating, wherein the bioactive metal are operable to be eluted at a rate of at least 0.25 µg/cm$^2$ 24 h$^{-1}$, for at least 14 consecutive days, in use, and wherein the titanium substrate having the bioactive metal deposited thereon is obtainable by contacting the titanium substrate with an 7 to 13M solution of a group I or group II metal hydroxide to thereby passivate the titanium substrate, then contacting the passivated titanium substrate with a bioactive metal material.

The orthopaedic implant comprising a titanium substrate may comprise one or more anchor points, operable to allow the implant to be anchored in place, in use. The or each anchor point may comprise apertures, which may have an internal thread therein, operable to allow the implant to be anchored in position by a screw, in use.

The or each anchor point may include protecting means operable to protect bioactive material deposited thereon during anchoring of the implant. The protecting means may include, for example, bushings.

The orthopaedic implant comprising a titanium substrate may include one or more surface feature operable to reduce the contact surface between the implant and the area to which the implant is inserted, in use.

The or each surface feature may include, for example, ribs, channels, recesses, and the like. In some embodiments, where the orthopaedic implant is generally elongated, the or each surface feature may include longitudinally extending ribs, longitudinally extending channels, longitudinally extending recesses and the like.

Advantageously, the surface features of the orthopaedic implant are suitably operable to reduce the surface area of the implant contacting the surrounding area (such as a bone tunnel) during insertion thereof, thereby reducing the risk of damage to the bioactive material on the implant upon insertion.

It will be appreciated that all of the features contained herein may be combined with any of the above aspects and in any combination. Certain elements of the present invention can be summarised by the following points. It will be appreciated that the subject matter of each point may be combined where appropriate with another point(s) and/or subject matter disclosed herein.

1. An orthopaedic implant comprising a titanium substrate having silver deposited thereon, wherein the silver is operable to be eluted at a rate of at least 0.25 µg/cm$^2$ 24 h$^{-1}$, for at least 14 consecutive days, in use.
2. An orthopaedic implant according to point 1, wherein the titanium substrate comprises silver ions and/or silver nanoparticles.
3. An orthopaedic implant comprising a titanium substrate having silver deposited thereon, and being coated with a polymeric coating, wherein the silver is operable to be eluted at a rate of at least 0.25 µg/cm$^2$ 24 h$^{-1}$, for at least 14 consecutive days, in use.
4. An orthopaedic implant according to point 3, wherein the titanium substrate comprises silver ions and/or silver nanoparticles.
5. An orthopaedic implant according to either of point 3 or point 4, wherein the polymeric coating comprises a polymer material.
6. An orthopaedic implant according to point 5, wherein the polymer material comprises a natural polymer, a synthetic polymer, or a combination thereof.
7. An orthopaedic implant according to either of point 5 or point 6, wherein the polymer material comprises hemaleucin, gelatin or a combination thereof.
8. An orthopaedic implant according to any of points 3 to 7, wherein the polymeric coating is applied to the orthopaedic implant by dip coating.
9. An orthopaedic implant according to point 8, wherein the dip coating comprises the steps of: (i) immersing the orthopaedic substrate in a coating solution comprising the polymeric material and a solvent, (ii) withdrawing the orthopaedic substrate from the coating solution to form a wet layer, and (iii) curing the polymeric coating.
10. An orthopaedic implant according to point 9, wherein the solvent comprises ethyl acetate, dimethyl carbonate, or combinations thereof.
11. An orthopaedic implant according to either of point 9 or point 10, wherein the polymeric material is present in the coating solution at a concentration of about 2.5 to 50% weight/volume (w/v).

12. An orthopaedic implant according to any of points 8 to 11, wherein the polymeric coating is applied to the orthopaedic implant by dip coating at a rate of about 20 to 500 mm/min.
13. An orthopaedic implant according to point 12, wherein the polymeric coating is applied to the orthopaedic implant by dip coating at a rate of about 50 mm/min.
14. An orthopaedic implant according to any of points 3 to 13, wherein the polymeric coating comprises a bioactive material, such as bioactive metal.
15. An orthopaedic implant according to point 14, wherein the bioactive material is silver.
16. An orthopaedic implant according to any of points 3 to 15, wherein the polymeric coating comprises one or more biofilm disrupting agent.
17. An orthopaedic implant comprising a titanium substrate having silver deposited thereon and having a polymer coating thereon, the polymer coating being applied to the titanium substrate having silver deposited thereon at a rate of between 10 mm/min and 1000 mm/min.
18. An orthopaedic implant according to point 17, wherein the titanium substrate comprises silver ions and/or silver nanoparticles.
19. An orthopaedic implant according to point 17 or 18, wherein the polymeric coating comprises a polymer material.
20. An orthopaedic implant according to point 19, wherein the polymer material comprises a natural polymer, a synthetic polymer, or a combination thereof.
21. An orthopaedic implant according to point 19 or 20, wherein the polymer material comprises hemaleucin, gelatin or a combination thereof.
22. An orthopaedic implant according to any of points 17 to 21, wherein the polymeric coating is applied to the orthopaedic implant by dip coating.
23. An orthopaedic implant according to point 22, wherein the dip coating comprises the steps of: (i) immersing the orthopaedic substrate in a coating solution comprising the polymeric material and a solvent, (ii) withdrawing the orthopaedic substrate from the coating solution to form a wet layer, and (iii) curing the polymeric coating.
24. An orthopaedic implant according to point 23, wherein the solvent comprises ethyl acetate, dimethyl carbonate, or combinations thereof.
25. An orthopaedic implant according to point 23 or 24, wherein the polymeric material is present in the coating solution at a concentration of about 2.5 to 50% weight/volume (w/v).
26. An orthopaedic implant according to any of points 23 to 25, wherein the polymeric coating is applied to the orthopaedic implant by dip coating at a rate of about 20 to 500 mm/min.
27. An orthopaedic implant according to point 26, wherein the polymeric coating is applied to the orthopaedic implant by dip coating at a rate of about 50 mm/min.
28. An orthopaedic implant according to any of points 17 to 27, wherein the polymeric coating comprises a bioactive material, such as bioactive metal.
29. An orthopaedic implant according to point 28, wherein the bioactive material is silver.
30. An orthopaedic implant according to any of points 17 to 29, wherein the polymeric coating comprises one or more biofilm disrupting agent.
31. An orthopaedic implant according to any of points 17 to 25 and 28 to 30, wherein the polymeric coating is deposited onto the titanium substrate having silver deposited thereon at a rate of between 30 mm/min and 500 mm/min, such as between 50 mm/min and 300 mm/min.
32. An orthopaedic implant comprising a titanium substrate having silver deposited thereon and having a polymeric coating thereon, the polymeric coating being operable to allow elution of the silver into the body at a rate at least 0.25 µg/cm$^2$ 24 h$^{-1}$, in use, and being obtainable by applying the polymer coating to the titanium substrate having silver deposited thereon at a rate of between 10 mm/min and 1000 mm/min.
33. An orthopaedic implant according to point 32, wherein the titanium substrate comprises silver ions and/or silver nanoparticles.
34. An orthopaedic implant according to either of point 32 or point 33, wherein the polymeric coating comprises a polymer material.
35. An orthopaedic implant according to point 34, wherein the polymer material comprises a natural polymer, a synthetic polymer, or a combination thereof.
36. An orthopaedic implant according to either of point 34 or point 35, wherein the polymer material comprises hemaleucin, gelatin or a combination thereof.
37. An orthopaedic implant according to any of points 32 to 36, wherein the polymeric coating is applied to the orthopaedic implant by dip coating.
38. An orthopaedic implant according to point 37, wherein the dip coating comprises the steps of: (i) immersing the orthopaedic substrate in a coating solution comprising the polymeric material and a solvent, (ii) withdrawing the orthopaedic substrate from the coating solution to form a wet layer, and (iii) curing the polymeric coating.
39. An orthopaedic implant according to point 38, wherein the solvent comprises ethyl acetate, dimethyl carbonate, or combinations thereof.
40. An orthopaedic implant according to either of point 38 or point 39, wherein the polymeric material is present in the coating solution at a concentration of about 2.5 to 50% weight/volume (w/v).
41. An orthopaedic implant according to any of points 37 to 40, wherein the polymeric coating is applied to the orthopaedic implant by dip coating at a rate of about 20 to 500 mm/min.
42. An orthopaedic implant according to point 41, wherein the polymeric coating is applied to the orthopaedic implant by dip coating at a rate of about 50 mm/min.
43. An orthopaedic implant according to any of points 32 to 42, wherein the polymeric coating comprises a bioactive material, such as bioactive metal.
44. An orthopaedic implant according to point 43, wherein the bioactive material is silver.
45. An orthopaedic implant according to any of points 32 to 44, wherein the polymeric coating comprises one or more biofilm disrupting agent.
46. An orthopaedic implant according to any of points 32 to 40 and 41 to 45, wherein the polymeric coating is deposited onto the titanium substrate having silver deposited thereon at a rate of between 30 mm/min and 500 mm/min, such as between 50 mm/min and 300 mm/min.
47. An orthopaedic implant comprising a titanium substrate having silver deposited thereon, wherein the silver is operable to be eluted at a rate of at least 0.25 µg/cm² 24 h⁻¹, for at least 14 consecutive days, in use, obtainable by subjecting the titanium substrate having silver deposited thereon to a heat treatment.
48. An orthopaedic implant according to point 47, wherein the titanium substrate comprises silver ions and/or silver nanoparticles.
49. An orthopaedic implant according to either of point 47 or point 48, wherein the heat treatment comprises exposing the titanium substrate having silver deposited thereon to an elevated temperature for a time period T.
50. An orthopaedic implant according to point 49, wherein the heat treatment comprises exposing the titanium substrate having silver deposited thereon to temperature of between 250 and 310° C. for a time period T.
51. An orthopaedic implant according to either of point 49 or point 50, wherein the time period T is at least 15 minutes.
52. An orthopaedic implant according to any one of points 47 to 51, wherein the orthopaedic implant comprising a titanium substrate having silver deposited thereon has a polymeric coating thereon.
53. An orthopaedic implant according to point 52, wherein the polymeric coating comprises a polymer material.
54. An orthopaedic implant according to point 52, wherein the polymer material comprises a natural polymer, a synthetic polymer, or a combination thereof.
55. An orthopaedic implant according to either of point 53 or point 54, wherein the polymer material comprises hemaleucin, gelatin or a combination thereof.
56. An orthopaedic implant according to any of points 52 to 55, wherein the polymeric coating comprises a bioactive material such as bioactive metal.
57. An orthopaedic implant according to point 56, wherein the bioactive material is silver.
58. An orthopaedic implant according to any of points 52 to 57, wherein the polymeric coating comprises one or more biofilm disrupting agent.
59. An orthopaedic implant comprising a titanium substrate having silver deposited thereon at an amount of at least 10 µg/cm².
60. An orthopaedic implant according to point 59, wherein the titanium substrate comprises silver ions and/or silver nanoparticles.
61. An orthopaedic implant comprising a titanium substrate having silver deposited thereon wherein the titanium substrate having the silver deposited thereon is obtainable by contacting the titanium substrate with a 7 to 13M solution of a group I or group II metal hydroxide to thereby passivate the titanium substrate, then contacting the passivated titanium substrate so obtained with a silver material.
62. An orthopaedic implant according to point 61, wherein the titanium substrate comprises silver ions and/or silver nanoparticles.
63. An orthopaedic implant according to either of point 61 or point 62, wherein the group I or group II metal hydroxide is selected from one or more of the following: lithium hydroxide, sodium hydroxide, potassium hydroxide, beryllium hydroxide, magnesium hydroxide or calcium hydroxide.
64. An orthopaedic implant according to any of points 61 to 63, wherein the solution of a group I or group II metal hydroxide has a molarity of between 8M and 12M.
65. An orthopaedic implant according to any of points 61 to 64, wherein the titanium substrate is contacted with the solution of a group I or group II metal hydroxide for a time period of at least 30 minutes.
66. An orthopaedic implant according to any of points 61 to 65, wherein the silver material comprises a silver salt.
67. An orthopaedic implant according to point 66, wherein the silver salt has a concentration of at least 0.01M.
68. An orthopaedic implant according to either of point 66 or point 67, wherein the silver salt comprises silver nitrate.
69. An orthopaedic implant comprising a titanium substrate having silver deposited thereon and over coated with a polymeric coating, wherein the silver is operable to be eluted at a rate of at least 0.25 µg/cm² 24 h⁻¹, for at least 14 consecutive days, in use, and wherein the titanium substrate having the silver deposited thereon is obtainable by contacting the titanium substrate with an 7 to 13M solution of a group I or group II metal hydroxide to thereby passivate the titanium substrate, then contacting the passivated titanium substrate with a silver material.
70. An orthopaedic implant according to point 69, wherein the titanium substrate comprises silver ions and/or silver nanoparticles.
71. An orthopaedic implant according to either of point 69 or point 70, wherein the polymeric coating comprises a polymer material.
72. An orthopaedic implant according to point 71, wherein the polymer material comprises a natural polymer, a synthetic polymer, or a combination thereof.
73. An orthopaedic implant according to either of point 71 or point 72, wherein the polymer material comprises hemaleucin, gelatin or a combination thereof.
74. An orthopaedic implant according to any of points 69 to 73, wherein the polymeric coating comprises a bioactive material such as bioactive metal.
75. An orthopaedic implant according to point 74, wherein the bioactive material is silver.
76. An orthopaedic implant according to any of points 69 to 75, wherein the polymeric coating comprises one or more biofilm disrupting agent.
77. An orthopaedic implant comprising a titanium substrate having silver deposited thereon, wherein the titanium substrate having silver deposited thereon is contacted with a blackening reducing agent.
78. An orthopaedic implant according to point 77, wherein the titanium substrate comprises silver ions and/or silver nanoparticles.
79. An orthopaedic implant according to either of point 77 or point 78, wherein the blackening reducing agent is selected from one or more of the following: polyvinylpyrrolidone, poly(vinyl alcohol), poly(ethylene glycol), sodium chloride, sodium sulphide, alkaline glucose, sodium citrate, ascorbate, poly (ethylene glycol)-block, sodium borohydride.
80. An orthopaedic implant according to point 78, wherein the blackening reducing agent comprises sodium sulphide.
81. An orthopaedic implant comprising a titanium substrate having silver deposited thereon, wherein the titanium substrate having silver deposited thereon is contacted with a blackening reducing agent, such as sodium sulphide, and wherein the silver is operable to be eluted at a rate of at least 0.25 µg/cm² 24 h⁻¹, for at least 14 consecutive days, in use.

82. An orthopaedic implant according to point 81, wherein the titanium substrate comprises silver ions and/or silver nanoparticles.

83. An orthopaedic implant comprising a titanium substrate having bioactive metal deposited thereon, wherein the bioactive metal is operable to be eluted at a rate of at least 0.25 µg/cm² 24 h⁻¹, for at least 14 consecutive days, in use.

84. An orthopaedic implant comprising a titanium substrate having bioactive metal deposited thereon, and being coated with a polymeric coating, wherein the bioactive metal is operable to be eluted at a rate of at least 0.25 µg/cm² 24 h⁻¹, for at least 14 consecutive days, in use.

85. An orthopaedic implant comprising a titanium substrate having bioactive metal deposited thereon and having a polymer coating thereon, the polymer coating being applied to the titanium substrate having bioactive metal deposited thereon at a rate of between 10 mm/min and 1000 mm/min.

86. An orthopaedic implant comprising a titanium substrate having bioactive metal deposited thereon and having a polymer coating thereon, the polymer coating being operable to allow elution of the bioactive metal into the body at a rate at least 0.25 µg/cm² 24 h⁻¹, in use, and being obtainable by applying the polymer coating to the titanium substrate having bioactive metal deposited thereon at a rate of between 10 mm/min and 1000 mm/min.

87. An orthopaedic implant comprising a titanium substrate having bioactive metal deposited thereon, wherein the bioactive metal is operable to be eluted at a rate of at least 0.25 µg/cm² 24 h⁻¹, for at least 14 consecutive days, in use, obtainable by subjecting the titanium substrate having bioactive metal deposited thereon to a heat treatment.

88. An orthopaedic implant comprising a titanium substrate having bioactive metal deposited thereon at an amount of at least 10 µg/cm².

89. An orthopaedic implant comprising a titanium substrate having bioactive metal deposited thereon wherein the titanium substrate having the bioactive metal deposited thereon is obtainable by contacting the titanium substrate with a 7 to 13M solution of a group I or group II metal hydroxide, then contacting the passivated titanium substrate so obtained with a bioactive metal material.

90. An orthopaedic implant comprising a titanium substrate having bioactive metal deposited thereon and over coated with a polymeric coating, wherein the bioactive metal are operable to be eluted at a rate of at least 0.25 µg/cm² 24 h⁻¹, for at least 14 consecutive days, in use, and wherein the titanium substrate having the bioactive metal deposited thereon is obtainable by contacting the titanium substrate with an 7 to 13M solution of a group I or group II metal hydroxide to thereby passivate the titanium substrate, then contacting the passivated titanium substrate with a bioactive metal material.

91. An orthopaedic implant according to any of points 83 to 90, wherein the bioactive metal is selected from one or more of the following: silver, gold, copper, tin, antimony, platinum, gallium, palladium, and zinc.

92. An orthopaedic implant according to any of points 83 to 91, wherein the bioactive metal deposited on the titanium substrate comprises bioactive metal ions and/or bioactive metal nanoparticles.

93. An orthopaedic implant substantially as described herein.

94. A method of preparing an orthopaedic implant substantially as herein described.

BRIEF DESCRIPTION OF THE DRAWINGS

For a better understanding of the invention, and to show how embodiments of the same may be carried into effect, reference will now be made, by way of example, to the following experimental data and figures, in which.

FIG. 15A shows a perspective view of a part of an orthopaedic implant having apertures therethrough;

FIG. 15B shows a perspective view of a part of an orthopaedic implant having apertures therethrough;

FIG. 16B shows a cross sectional view through the orthopaedic implant shown in FIG. 16a;

DETAILED DESCRIPTION

Examples

Figure 1:
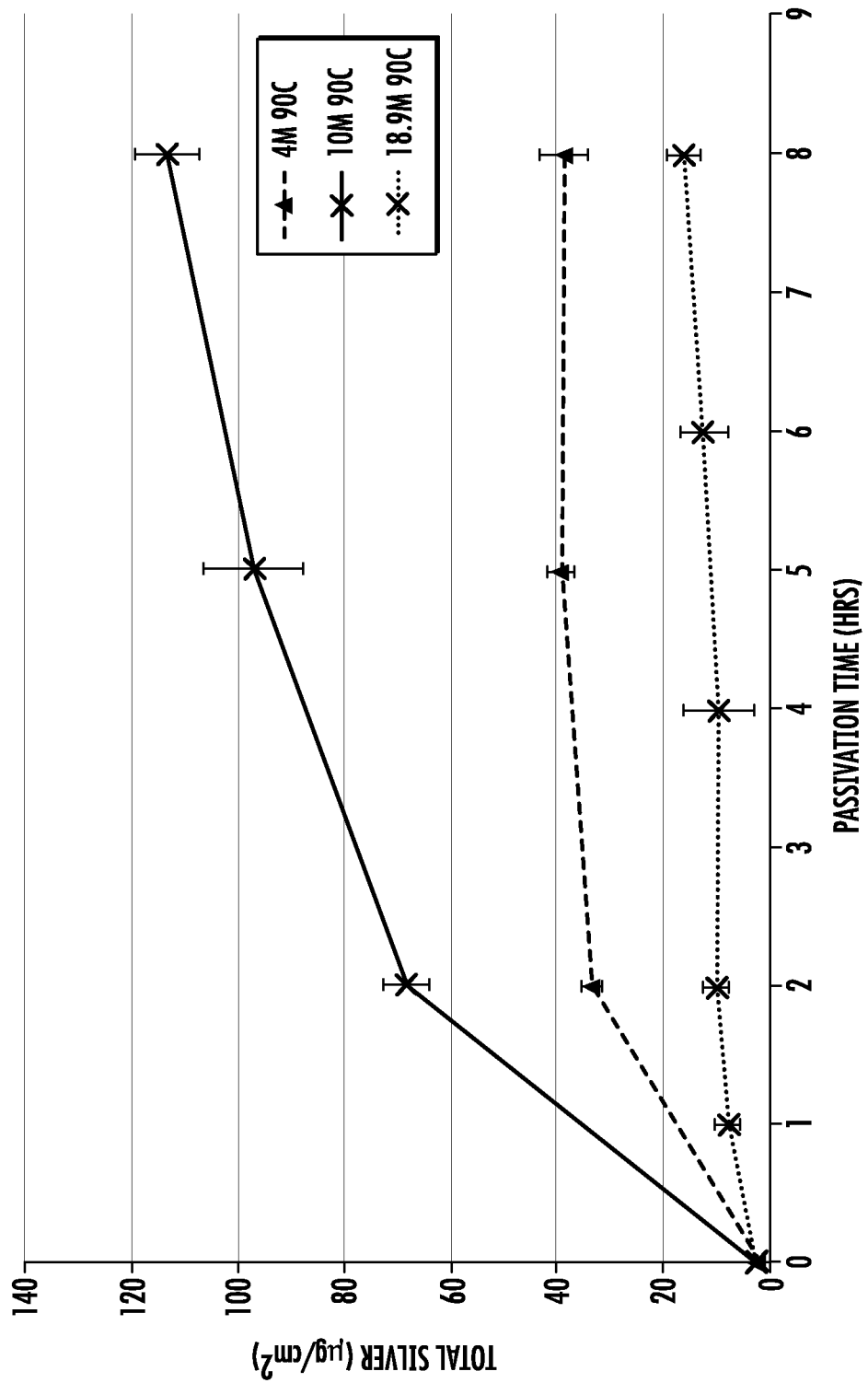
FIG. 1 shows a graph of experimental data relating to alkali passivation of titanium coupons carried out at different molarities.

Cylindrical coupons in two sizes (8.5 mm diameter×40 mm long) and (2 mm diameter×85 mm long) made from implant grade titanium-64 alloy were manufactured for the purpose of identifying a set of process conditions that could be transferrable to the final product such as, for example, an intramedullary nail with typical dimensions (i.e., 10 mm diameter×30 cm long). The surface finish of the coupons was also carefully controlled and resembled the final product (i.e., a 32 Ra micro-inch produced using either a dry or wet blast process). Surface roughness has a significant impact on the efficiency of the titanate process with a 32 Ra micro-inch grit blasted surface increasing the amount of silver by 33% compared to a machined surface. The coupons were subsequently washed and laser marked for identification.

Alkali Passivation

The prepared titanium implant is then subjected to alkali passivation by immersing the titanium intramedullary nail in a group I or group II metal hydroxide solution, such as, for example, sodium hydroxide or potassium hydroxide.

It has been found by the present invention that the alkali passivation step has a significant effect on silver loading. While not wishing to be bound by theory, it is considered that the alkali passivation step may be operable to control the microstructure of the ion exchangeable titanate. In particular, it has been found that the molarity of the metal hydroxide solution and the temperature both have a surprising and unexpected impact on the silver loading achieved.

Molarity of Alkali Agent

Alkali passivation of a titanium coupon was carried out at three different molarities: 4M, 10M and 18.9M NaOH several times, for differing amounts of time, up to 8 hours. These coupons were each rinsed and then immersed in 0.1M silver nitrate at 60° C. for 1 hour. Silver loading (in $\mu m/cm^2$) was then determined using ICP-MS. The standard test method for the characterization of materials for medical devices can be sourced from "Chemical Characterisation of Materials" as per ISO 10993:2005, Part 18, where acid digestion was used to strip silver from the coupon, and Inductively Coupled Mass Spectroscopy (ICP MS) was used as the test method to determine the silver content. ICP MS is a well-established technique and would be well known to a person skilled in the art. Briefly, coupons were immersed in 10 ml of a 2:1 nitric acid:deionised water solution and left overnight. Then, the solutions were mixed by vortex and serially diluted 1,000× with a 1% solution of nitric acid. The diluted solutions were analysed using ICP MS to quantify the silver content under the following conditions: instrument—Agilent 8800 ICP-MS triple quad; autosampler—ASX-500 series; sample introduction—peri pump; nebuliser—micro mist; lens type—x; scan—single quad; plasma mode—general purpose; acquisition mode—spectrum; spectrum mode options—Q2 peak patterns 3 points, 3 reps, 100 sweeps/rep; elements—Rh (IS) (mass 103, int. time 0.3 s), Ag (mass 107, int. time 0.3 s).

The results are shown in FIG. 1, wherein the silver loading at 10M NaOH is surprisingly and unexpectedly significantly higher than the silver loading at 4M NaOH or 18.9M NaOH.

Temperature of Alkali Passivation Step

Alkali passivation of the titanium coupons was carried out at 60° C. and at 90° C. several times, for differing amounts of time, up to 8 hours. These parts were then rinsed and immersed in 0.1M silver nitrate at 60° C. for 1 hour. Silver loading (in $\mu m/cm^2$) was then determined using ICP-MS.

Figure 2:
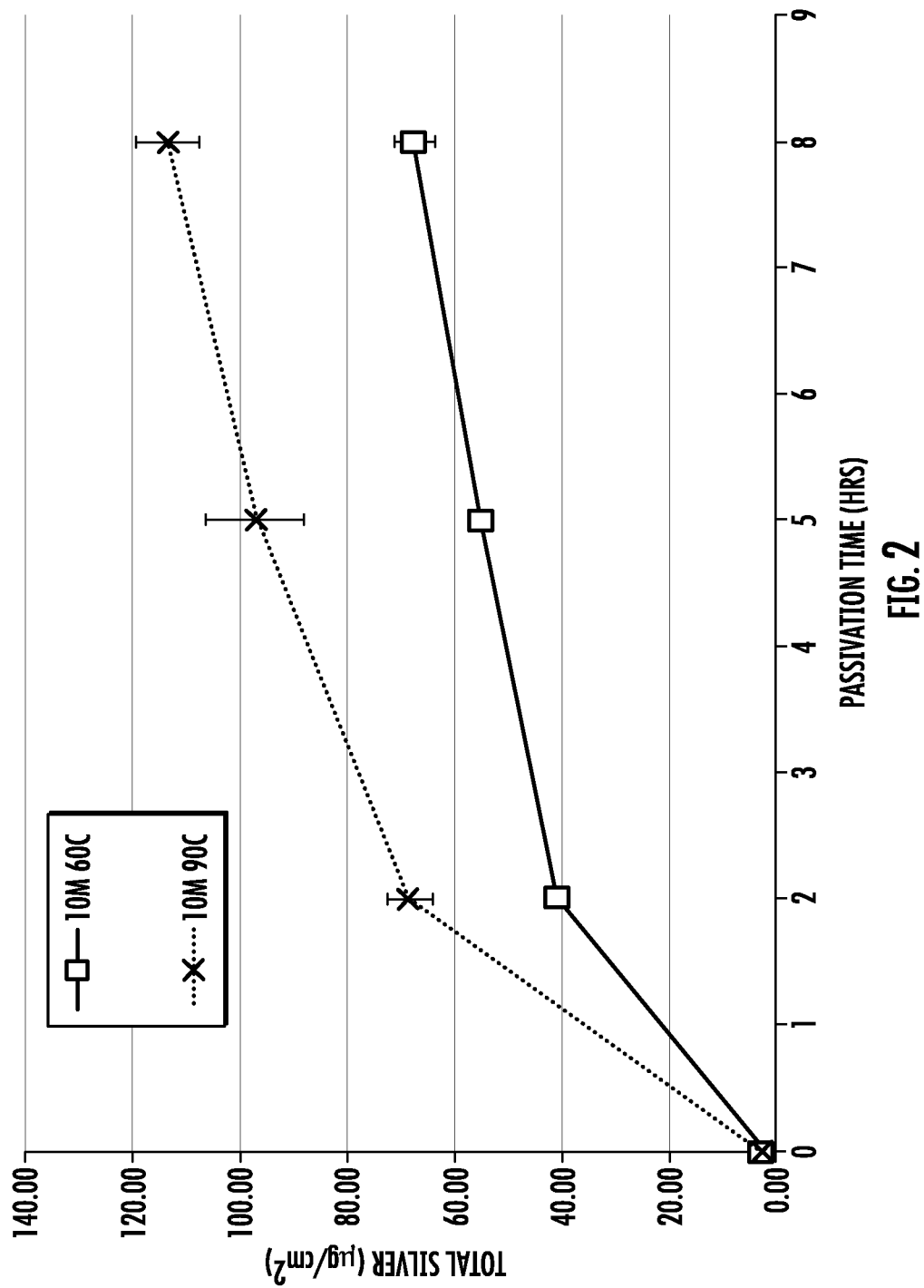
FIG. 2 shows a graph of experimental data relating to alkali passivation of titanium coupons carried out at differing temperatures.

The results are shown in FIG. 2, wherein it can clearly be seen that passivation at 90° C. had a significant beneficial effect on the silver loading.

Colour Improvement

The deposited silver nano particles (AgNP's) are prone to oxidation under ambient conditions, and also when dried in presence of air/oxygen. On long standing, they can also turn black due to the pick-up of impurities, such as oxygen and silver, due to the large surface area of the AgNP's, which exposes the loosely held outermost electrons to these species. Once de-stabilized, it is generally very difficult to re-disperse the AgNP's because of the high surface to volume ratio.

In order to control the appearance before or after gamma or ETO sterilization, the silver titanate parts can be subjected to chemical stabilisation using either capping agents (polyvinylpyrrolidone, poly(vinyl alcohol), poly(ethylene glycol), or reducing agents (sodium chloride, sodium sulphide, alkaline glucose, sodium citrate, ascorbate, poly (ethylene glycol)-block, sodium borohydride). The reducing agents reduce silver ions in aqueous or non-aqueous solutions to metallic silver, which is followed by agglomeration into oligomeric clusters. The capping agents stabilize particle growth, and protect particles from sedimentation and agglomeration. Alternatively, non-chemical strategies for stabilizing the appearance of silver titanate include heat treatment (typically 280° C. for 2 hours) and UV photochemical reduction.

In one experiment, silver titanate treated parts were subject to treatment with either 2.5% w/v PVP, 10 k Mwt, 2.5% w/v PVP 40 k Mwt, 0.1 Mol $dm^{-3}$ NaCl, and 2.5% w/v alkaline glucose for 1 hour. In the case of glucose treatment, the part turned black after five (5) minutes prior to sterilization. The other treatments produced a lighter grey appearance comparable to the control (i.e., non-chemically treated titanate).

After gamma sterilization, all parts turned black with the exception of the parts that were treated with 0.1 Mol $dm^{-3}$ NaCl sodium chloride for 1 hour. These parts turned dark grey, which could in turn improve the visibility of laser markings for a final product.

Figure 3:
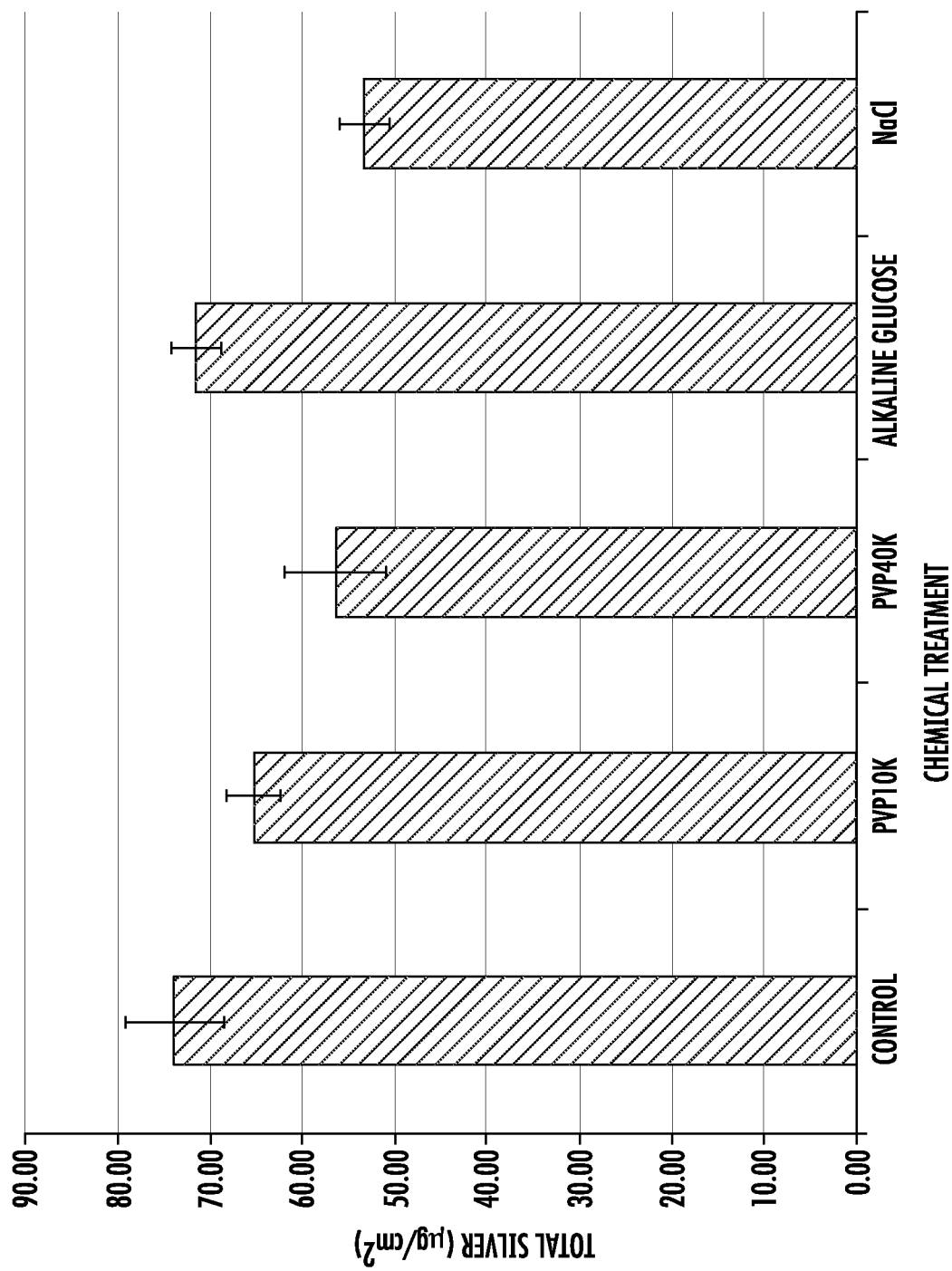
FIG. 3 shows a bar chart of experimental data relating to silver titanate treated parts subject to treatment with various reagents.

In this first set of experiments, the grit blasted test coupons were subjected to these chemical agents for 30 minutes. Sodium chloride was the only chemical treatment that retarded the black colour from the first set of experiments. However, as shown in FIG. 3, the level of silver dropped by 25% with this reagent.

Figure 4:
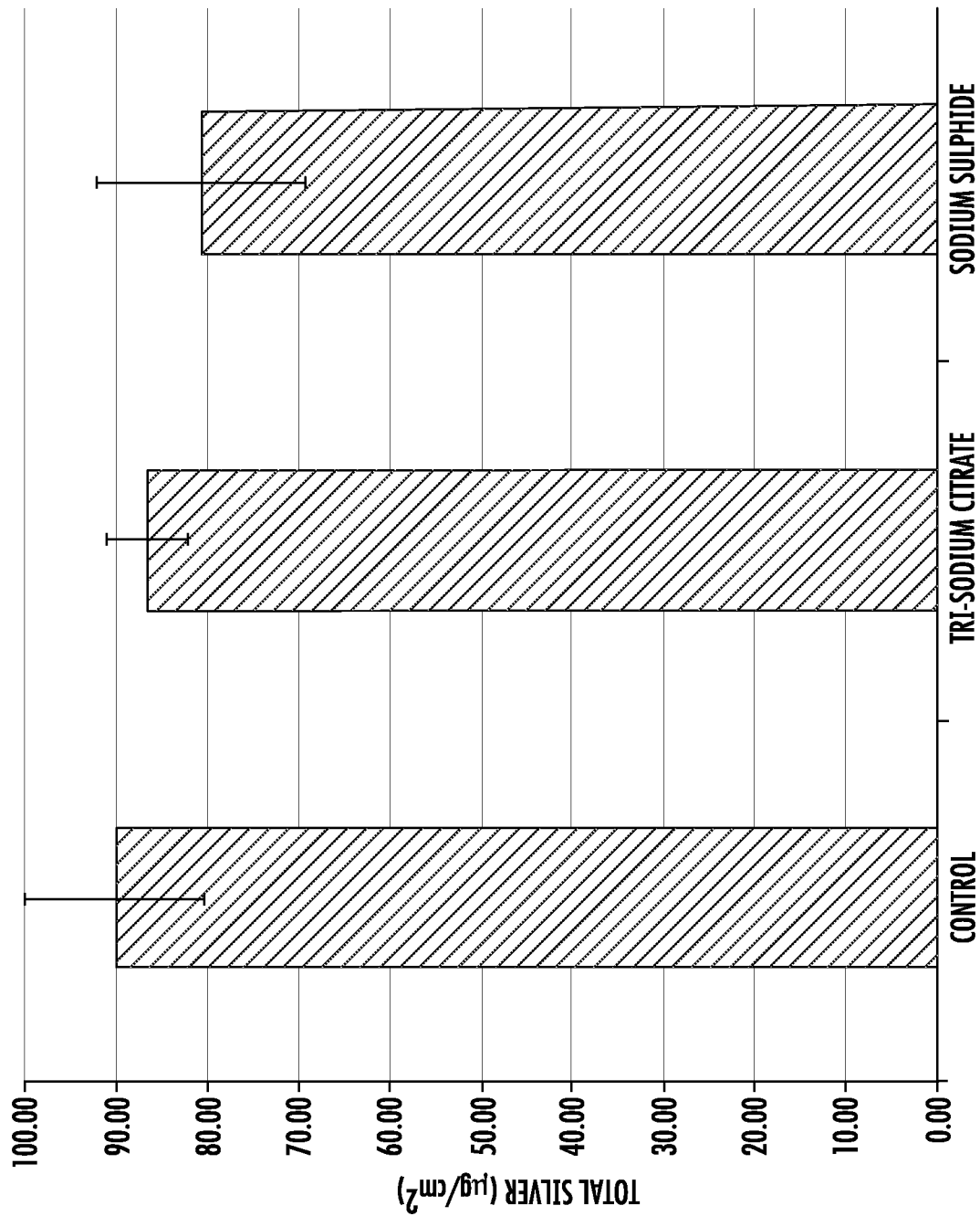
FIG. 4 shows a further bar chart of experimental data relating to silver titanate treated parts subject to treatment with various reagents.

In the second experiment, the silver titanate treated test coupons were subject to sodium 0.1M citrate and 0.1M sodium sulphate solutions for 30 minutes. The sodium sulphate treatment was found to retard the dark colour change after gamma sterilization. In addition, the amount of silver lost after this chemical treatment was negligible, as shown in FIG. 4.

The next set of experiments involved the use of laser marked cylindrical Ti-64 coupons. The coupons were passivated and silver treated, followed by chemical stabilization with 0.1M sodium sulphide treatment for up to 30 minutes. The non-chemically stabilized coupons exhibited a dark grey colour prior to sterilization. The coupon subjected to the chemical stabilisation agent turned a darker grey. In all cases, the laser markings were clearly discernible from the background metal. Post gamma sterilization, the control coupons darkened in colour. However, the coupons treated in sodium sulphide remained dark grey. In all cases, the laser markings were discernible from the base metal.

Figure 5:
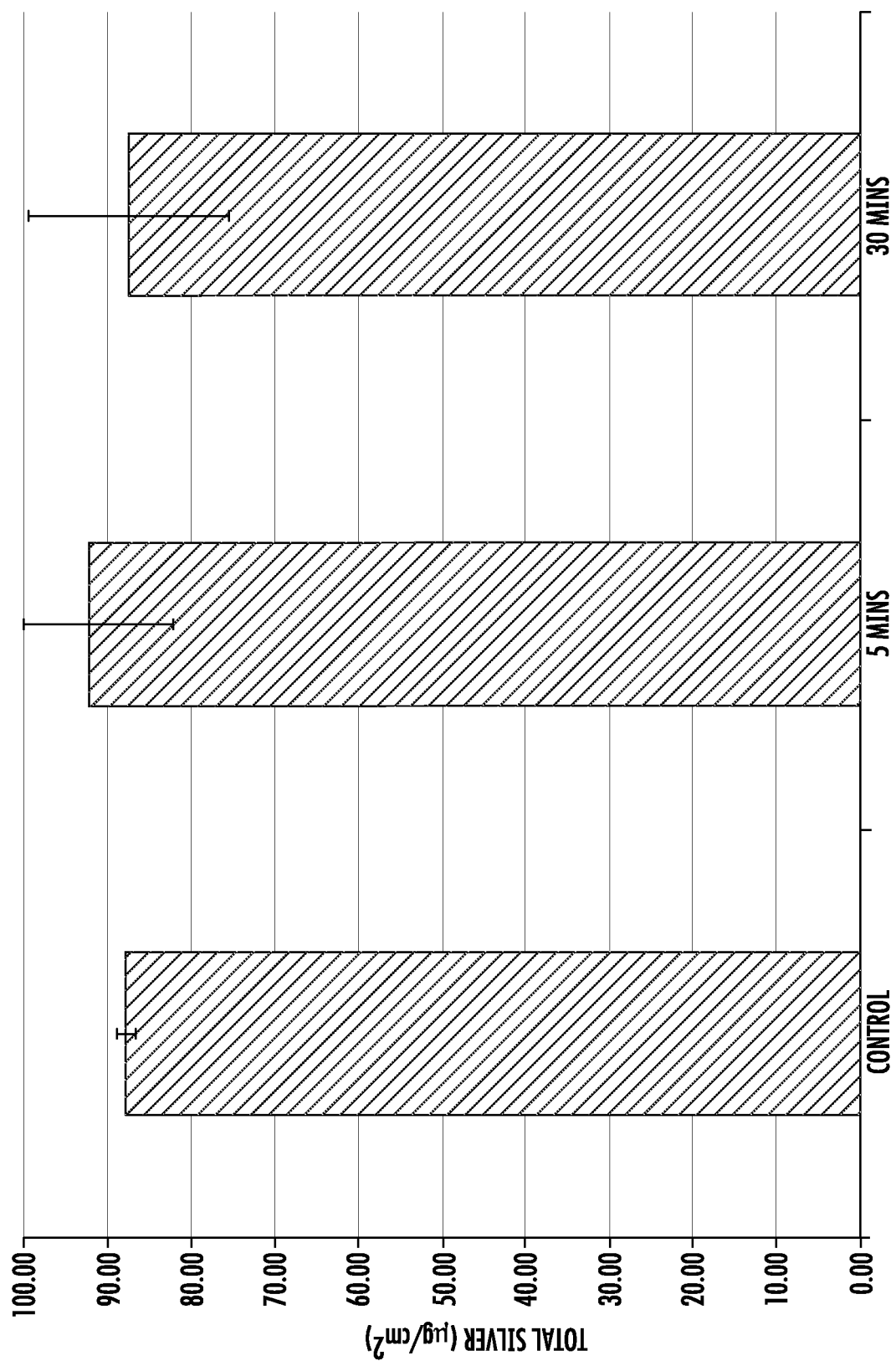
FIG. 5 shows a bar chart of experimental data relating to silver titanate treated parts subject to treatment with sodium sulphide.

Treatment with 0.1M sodium sulphide for five (5) and thirty (30) minutes did not have a significant effect on total silver, as indicated in FIG. 5.

For comparative purposes, silver titanate laser marked coupons subject to chemical stabilisation with 4 g/L sodium chloride were submitted for gamma sterilization. Prior to sterilization, all parts had a grey appearance and the laser markings could be read from each coupon. Post gamma sterilization, the five (5) and thirty (30) minute sodium chloride treatments produced a lighter shade of grey. However, the laser markings were discernible from the base metal in all cases.

Figure 6:
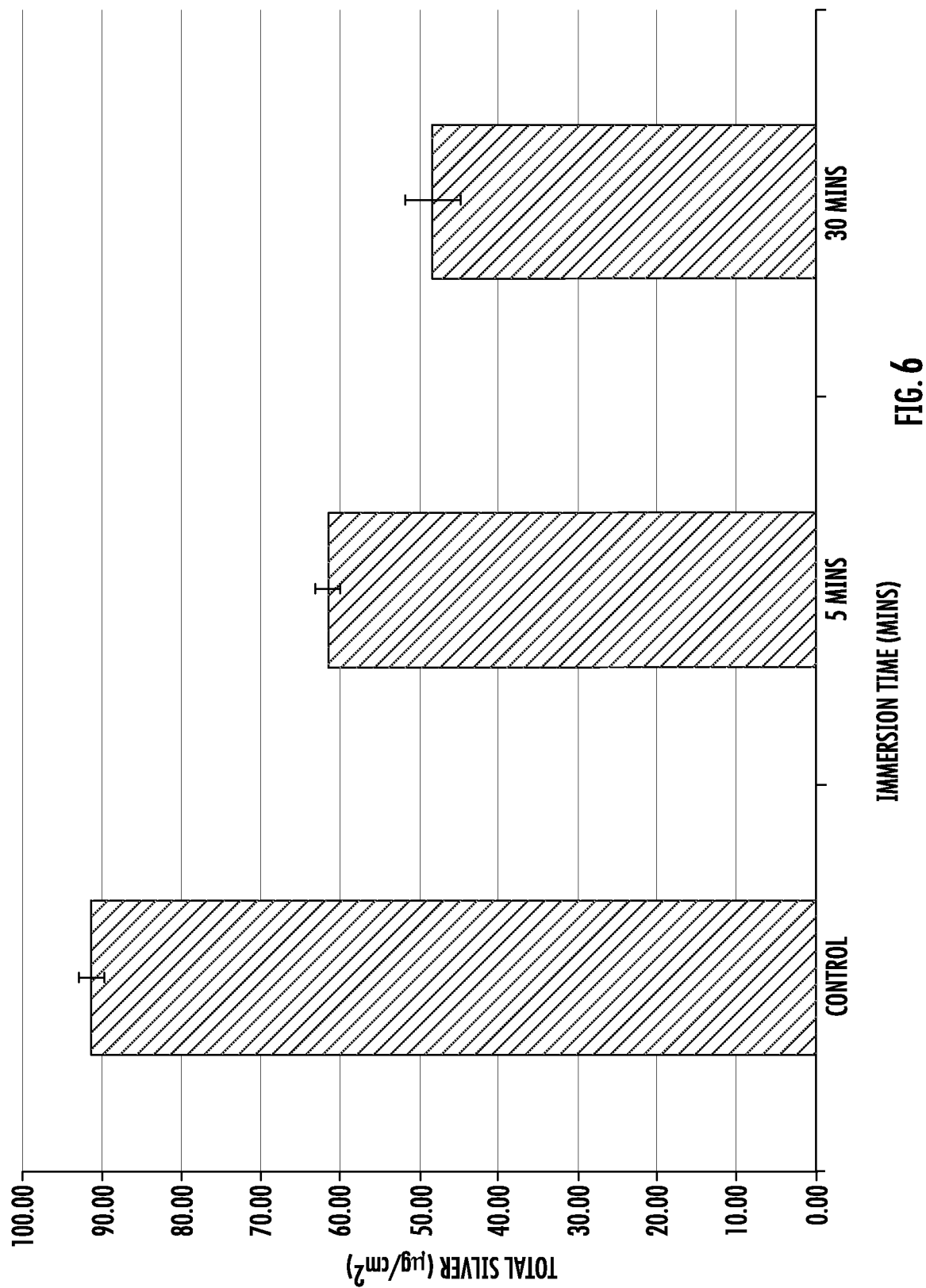
FIG. 6 shows a bar chart of experimental data relating to immersing silver titanate treated parts in 4 g/l sodium chloride.

Increasing the immersion time in 4 g/l sodium chloride resulted in a decrease in silver level from 91 to 48 $\mu g/cm^2$, as shown in FIG. 6. Accordingly, the use of sodium sulphide allows the colour to be controlled such that the laser markings are still visible, but without significant loss of silver.

Determination of Elution Profile

In order to determine the rate of elution of silver ions required to prevent attachment to the surface of a silver coated intramedullary nail in its intended environment (i.e., a bone canal), it is important to know the concentration of silver ions sufficient to keep it free from microbial contamination. In estimating this minimum silver ion elution rate, it was assumed that a small boundary layer around the implant needs to contain sufficient silver ions to kill any bacteria.

Figure 7:
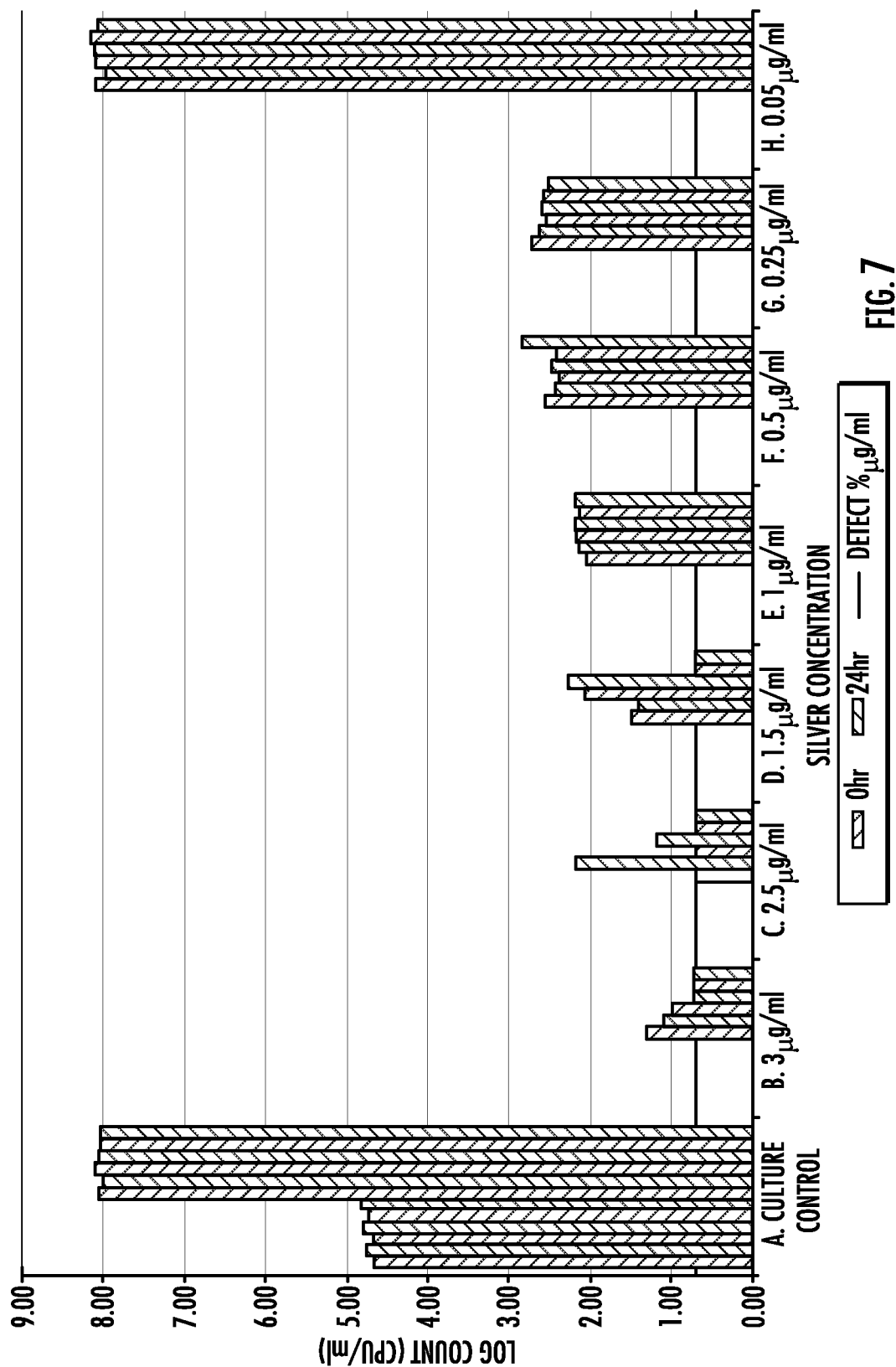
FIG. 7 shows a bar chart of experimental data relating to concentration of silver ions in the boundary layer required to kill each of S. aureus or eMRSA.
Figure 8:
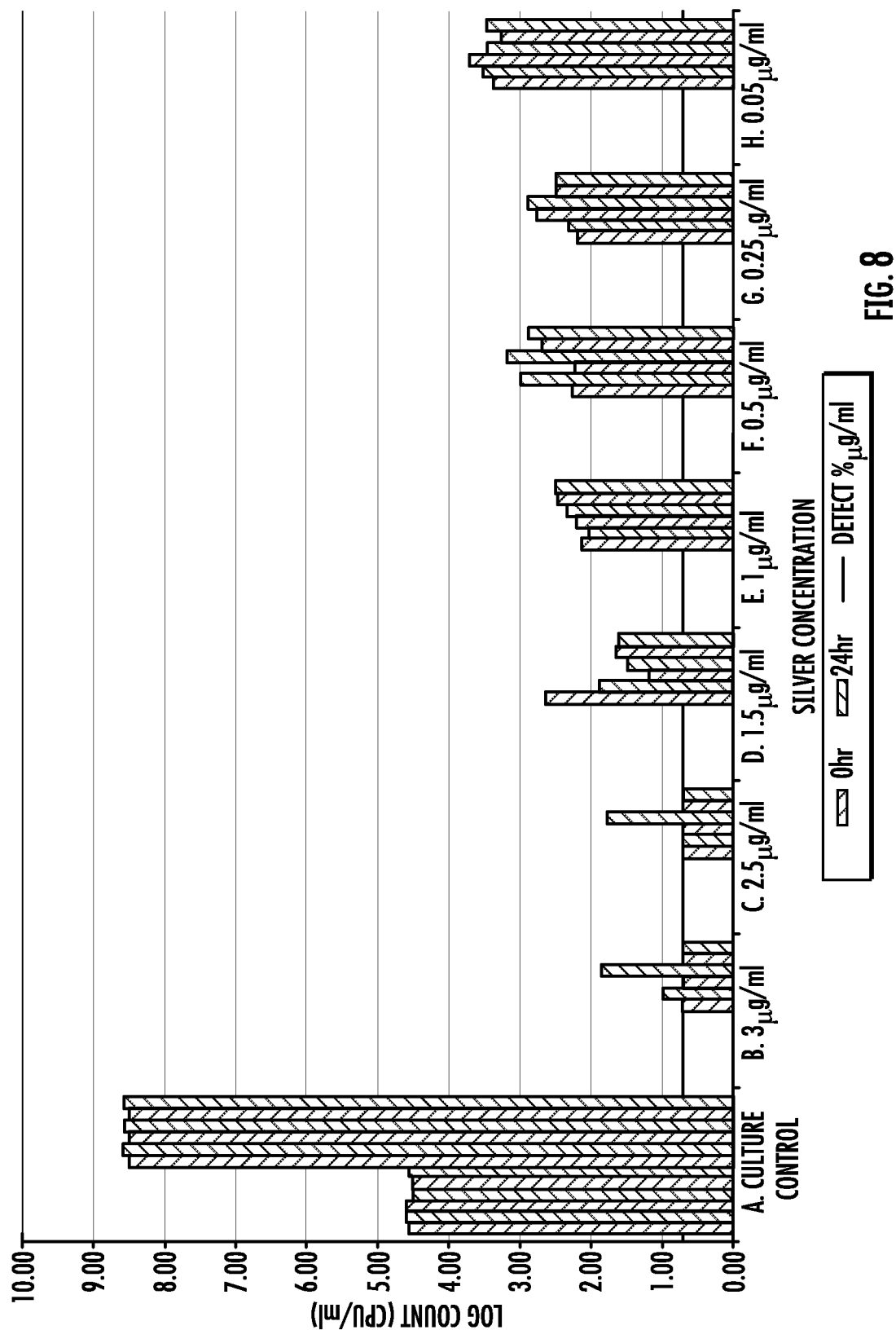
FIG. 8 shows a bar chart of experimental data relating to concentration of silver ions in the boundary layer required to kill each of S. aureus or eMRSA.

Tests were conducted to find the concentration of silver ions in the boundary layer required to kill each of S. aureus or eMRSA. Silver ions were added to cultures of each of S. aureus or eMRSA at differing solutions of between 0.05 and 5 μg/ml. This data is shown in FIGS. 7 and 8 where each bar represents one sample. Based on this data, a silver concentration of 2.5 $\mu g/cm^2$ was selected as at this silver ion concentration, greater than 50% of the experiments had the microbial count reduced to below the detection limit of 0.7 CFU/ml (colony-forming units per ml) at 24 hours. The detection limit corresponds to an approximate 4 log reduction in microbial count. Using this value, we calculate that the silver ions elution rate required to achieve this concentration is 0.25 g/cm2/day. If we assume that the silver is bound up by biological proteins, chlorides and/or cleared daily then this needs to be re-eluted daily suggesting an estimated minimum elution rate of 0.25 g/cm2/day.

Elution Control by Use of a Polymeric Coating

Alkali passivation of the titanium test coupons was carried out in a 10M sodium hydroxide solution at 90° C. for 12 hours. The parts were then rinsed and immersed in 0.1M silver nitrate at 60° C. for 1 hour. Silver loading (in $\mu g/cm^2$) was determined by the method described above to be approximately 105 $\mu g/cm^2$. Polymeric coatings were then added to the passivated parts by dip coating.

Figure 9:
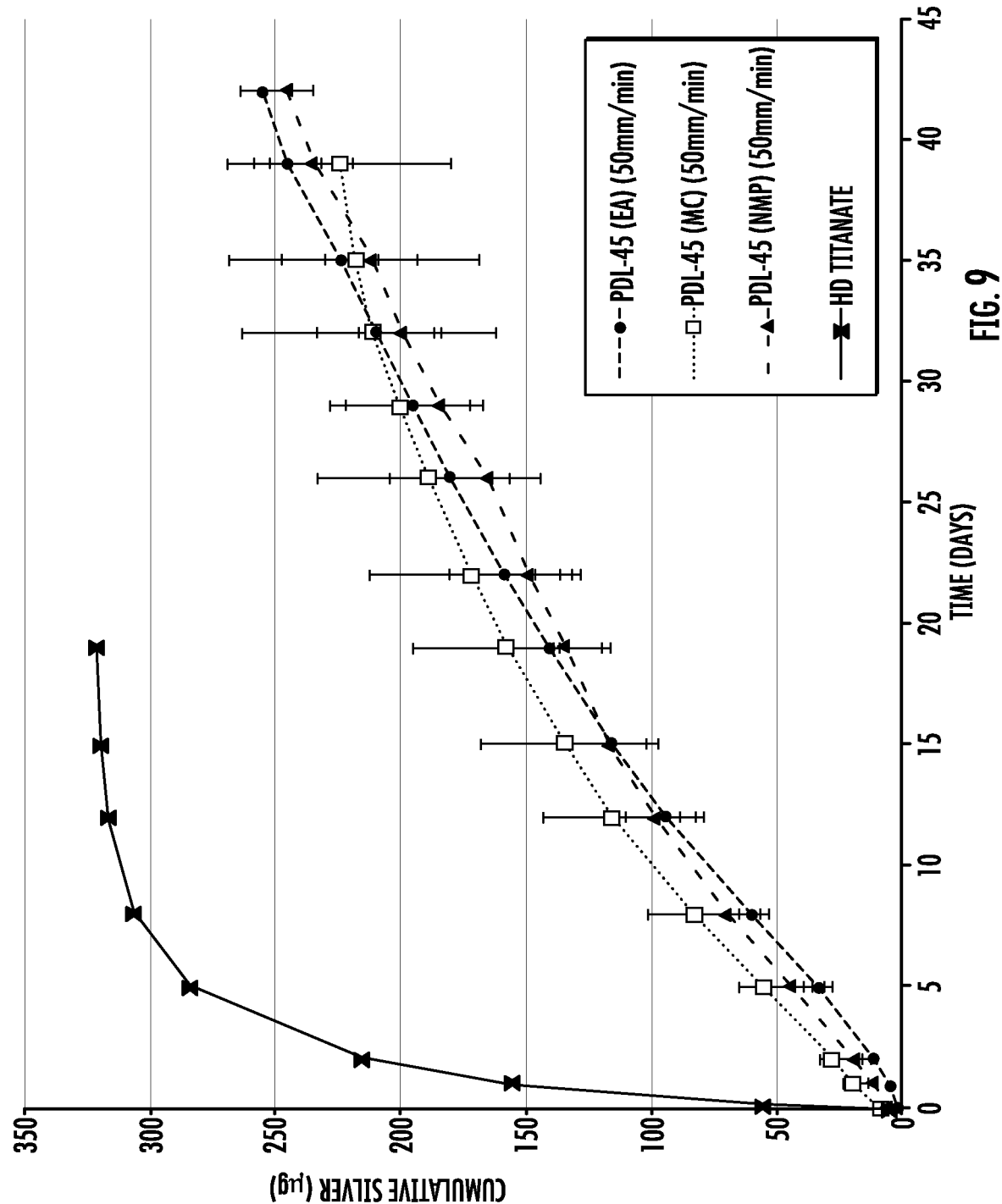
FIG. 9 shows a graph of experimental data relating to the rate of elution of silver ions from nails having polymeric coatings thereon.

In one experiment, the effect of different solvents was investigated. The silver titanate treated test coupons were dip coated in a 3.3% weight/volume (w/v) solution of PURASORB PDL 45 (a poly-D, L-lactide commercially available from Corbion), in several solvents, at a rate of 50 mm/minute. The solvents used were ethyl acetate, methylene chloride and N-methyl-2-pyrrolidone. The rate of elution of silver ions from nails having polymeric coatings thereon was reduced compared to those having no polymeric coating, as shown in FIG. 9. With all three solvents, the elution rate of silver was controlled by the addition of the polymeric coating extending the release phase to approximately two (2) months. In contrast, the non-coated silver titanate nails only eluted silver ions for about one (1) week.

Figure 10:
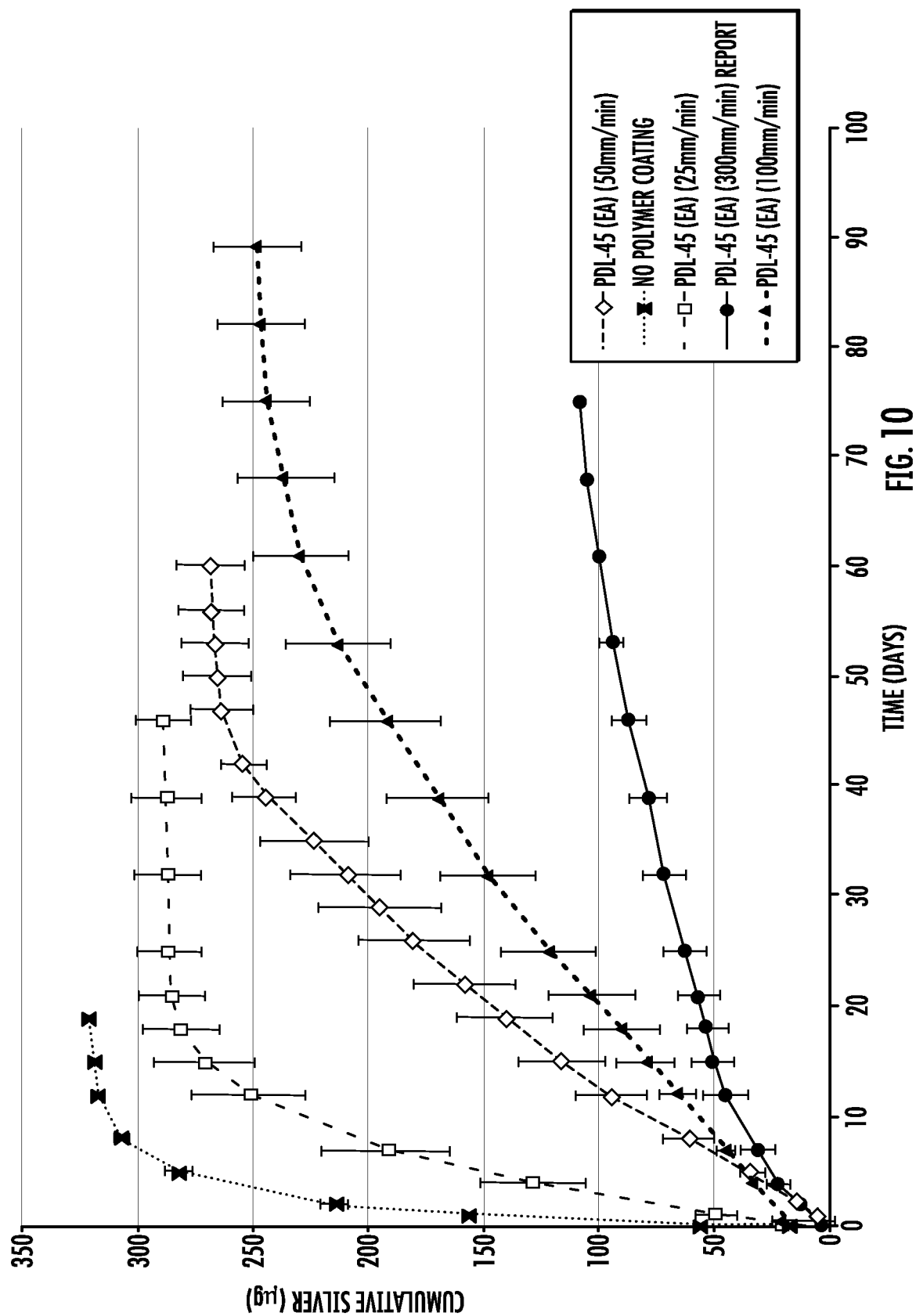
FIG. 10 shows a graph of experimental data relating to the rate of elution of silver ions from nails having polymeric coatings thereon.

In a further experiment, silver titanate treated test coupons were dip coated in a 3.3% weight/volume (w/v) solution of PURASORB PDL 45 (a poly-D,L-lactide commercially available from Corbion) in ethyl acetate at differing rates of between 25 and 300 mm/minute. Increasing the dipping speed reduces the rate of elution of silver ions, as shown in FIG. 10. It was also found that the coating thickness was increased when the dip coating speed was increased, as measured using an optical film analyser system (F40 available from Filmetrics Instruments). The elution rate of the polymeric coating applied at 300 mm/min has the potential to release silver over three (3) months.

Figure 11:
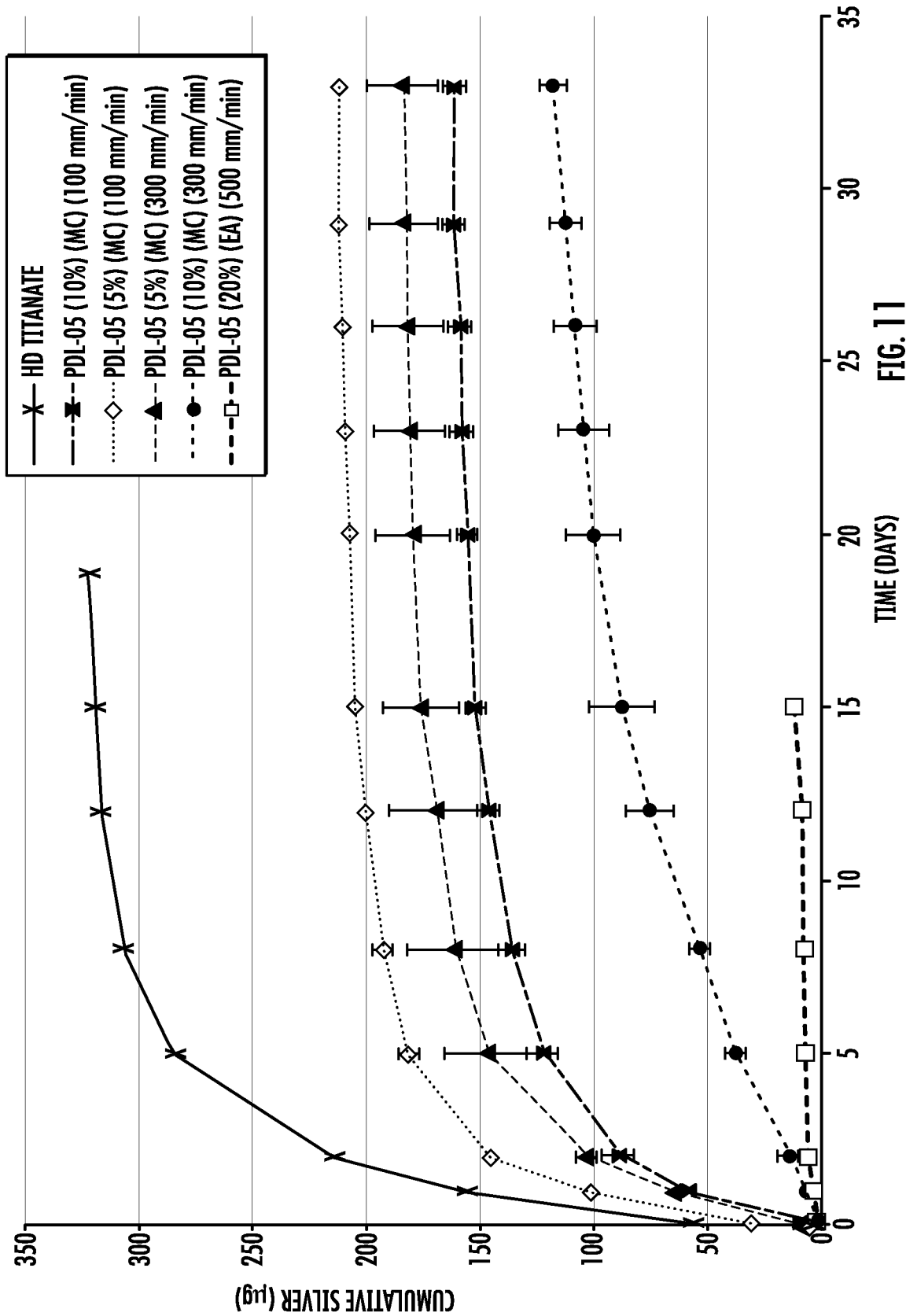
FIG. 11 shows a graph of experimental data relating to the rate of elution of silver ions from nails having polymeric coatings thereon.

In a further experiment, silver titanate treated test coupons were dip coated in a solution of a lower molecular weight polymer (PURASORB PDL-05, a poly-D, L-lactide commercially available from Corbion) in ethyl acetate at concentrations of 5, 10 and 20% w/v and at a rate of 100, 300 or 500 mm/minute. The elution rate of silver decreased when either the polymer concentration was increased from 5 to 30% w/v, or the dip coating speed was increased from 100 to 300 mm/min. This is shown in FIG. 11. The 20% w/v solution dipped at a rate of 500 mm/minute could elute silver for 420 days based on extrapolated elution data at 15 days.

Effect of Polymer Coating on In Vitro Cytotoxicity of Silver Titanate

In another experiment, the cytotoxicity of silver titanate treated nails dip coated with a poly-D,L-lactide polymer PDL-45 (3.3 wt % dipped at 100 mm/min) commercially available from Corbion) towards osteoblast MC3T3 cells was tested using the WST-1 assay. The results are shown in Table 1 below. Cytotoxic potential is shown with viability below 70%. Test coupons coated with poly-D, L-lactide significantly increased cell viability with no evidence of cytotoxicity. This data suggests that a polymer coating is a viable option for increasing the silver concentration in the titanate nanostructure without increasing the risk of toxicity.

TABLE 1

|  | MEAN cell viability | SD |
|---|---|---|
| Sodium titanate | 117.8 | 45.4 |
| Silver Titanate | 23.3 | 0.7 |
| silver titanate + polymer coating | 88.9 | 3.73 |

Effect of a Controlled Release Coating on In Vivo Bacterial Colonization

Figure 12:
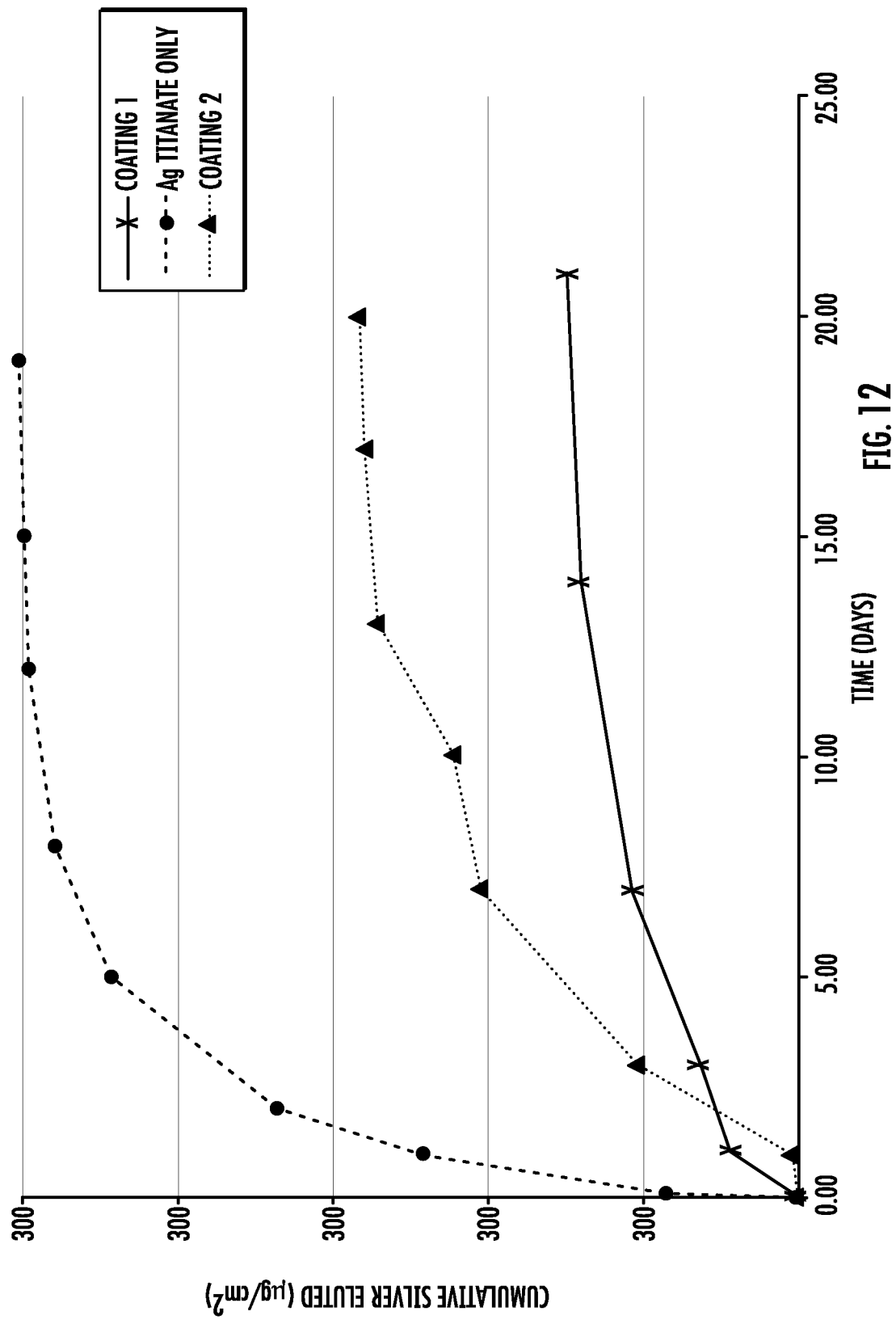
FIG. 12 shows a graph of experimental data relating to the rate of elution of silver ions from nails having polymeric coatings thereon.

In one experiment, two (2) week rabbit liquid inoculation infection studies were carried out on silver titanate test coupons, loaded at differing dosage levels of 50 µg/cm² (study 1) and 100 µg/cm² (study 2) to determine whether a controlled release of local antimicrobial agent prevented bacterial colonization of the implant. This localized tibial osteomyelitis model provides a longitudinal assessment of early post-operative implant infections involving *Staphylococcus aureus* and an indication of the clinical rate of infection. The silver titanate treated parts were dip coated with differing polymeric coatings. The results are shown in Table 2 below. The in vitro elution rate of coated and polymer coated silver titanate treated pins of the two rabbit studies is shown in FIG. 12.

Pins dosed at 50 µg/cm² without a polymer coating did not have any impact on reducing bacterial colonization, and had a bacterial colonization rate greater than the control pin (passivated titanium). Increasing the dosage of silver from 50 to 100 µg/cm² without the polymer coating reduced the bacterial colonization rate to 71.4%. Applying a dip coated polymer (coating 1; PURASORB PDL-02, a poly-D, L-lactide commercially available from Corbion) reduced the bacterial colonization rate to 43%. Pins dosed at 100 µg/cm² were also dip coated in PURASORB PDL-45 polymer (a poly-D, L-lactide commercially available from Corbion) at a dipping speed of 80 mm/minute. The implants coated at this dipping speed had a colonization rate of 64%.

Coating 1, which exhibited the slowest elution rate, produced the lowest rate of bacterial colonization rate. Coating 2, which produced a faster elution rate, produced a higher rate of bacterial colonization rate. The non-coated pins exhibited the highest rate of bacterial colonization rate.

TABLE 2

| Formulation | Study | Time-point (weeks) | Inoculation Dosage | Colonization Rate (Control) | Colonization Rate (Silver Group) |
|---|---|---|---|---|---|
| Silver Titanate (100 µg/cm²) | 1 | 2 | 10⁵ cfu (600 µl) | 6/7 (86%) | 5/7 (71.4%) |
| Silver Titanate (50 µg/cm²) | 1 | 2 | 10⁵ cfu (600 µl) | 6/7 (86%) | 7/7 (100%) |
| Silver Titanate (50 µg/cm²) + coating 1 | 1 | 2 | 10⁵ cfu (600 µl) | 6/7 (86%) | 3/7 (43%) |
| Silver Titanate (100 µg/cm²) + coating 2 | 2 | 2 | 10⁵ cfu (600 µl) | 10/11 (91%) | 7/11 (64%) |

Influence of Heat Treatment on Elution Behaviour of Silver Titanate

Figure 13:
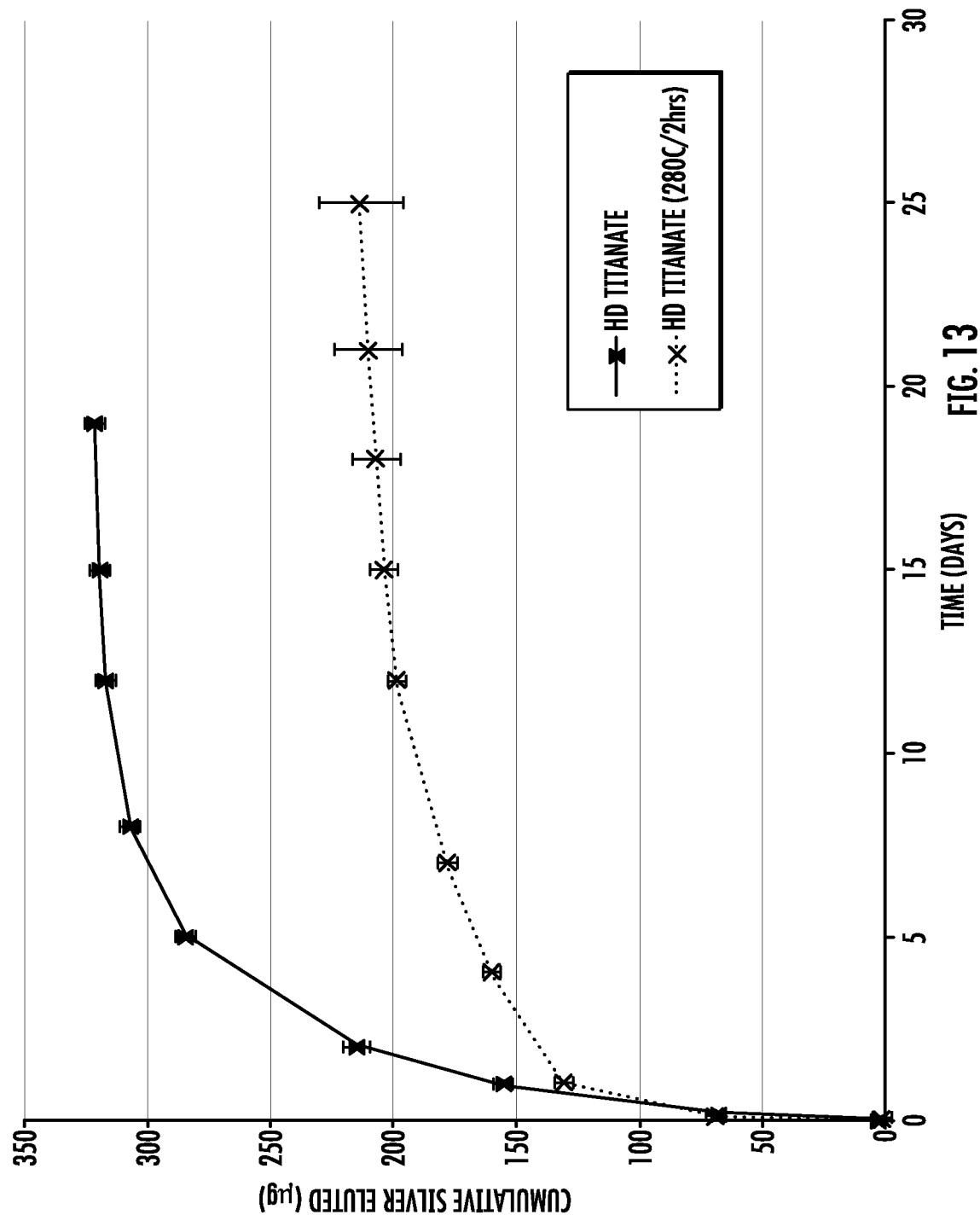
FIG. 13 shows a graph of experimental data relating to the rate of elution of silver ions from nails having polymeric coatings thereon.

Silver treated titanium parts prepared as described above in relation to test parts used in the rabbit infection study were heat treated at 280° C. for two (2) hours, resulting in a reduction in rate of elution of silver ions compared to the non-heat-treated parts. This is shown in FIG. 13. At 19 days, 96% of the silver was eluted from the silver titanate treated pins, whereas, in contrast, only 64% of the silver was eluted from the heat-treated pins after 25 days, as also shown in FIG. 13.

Figure 14:
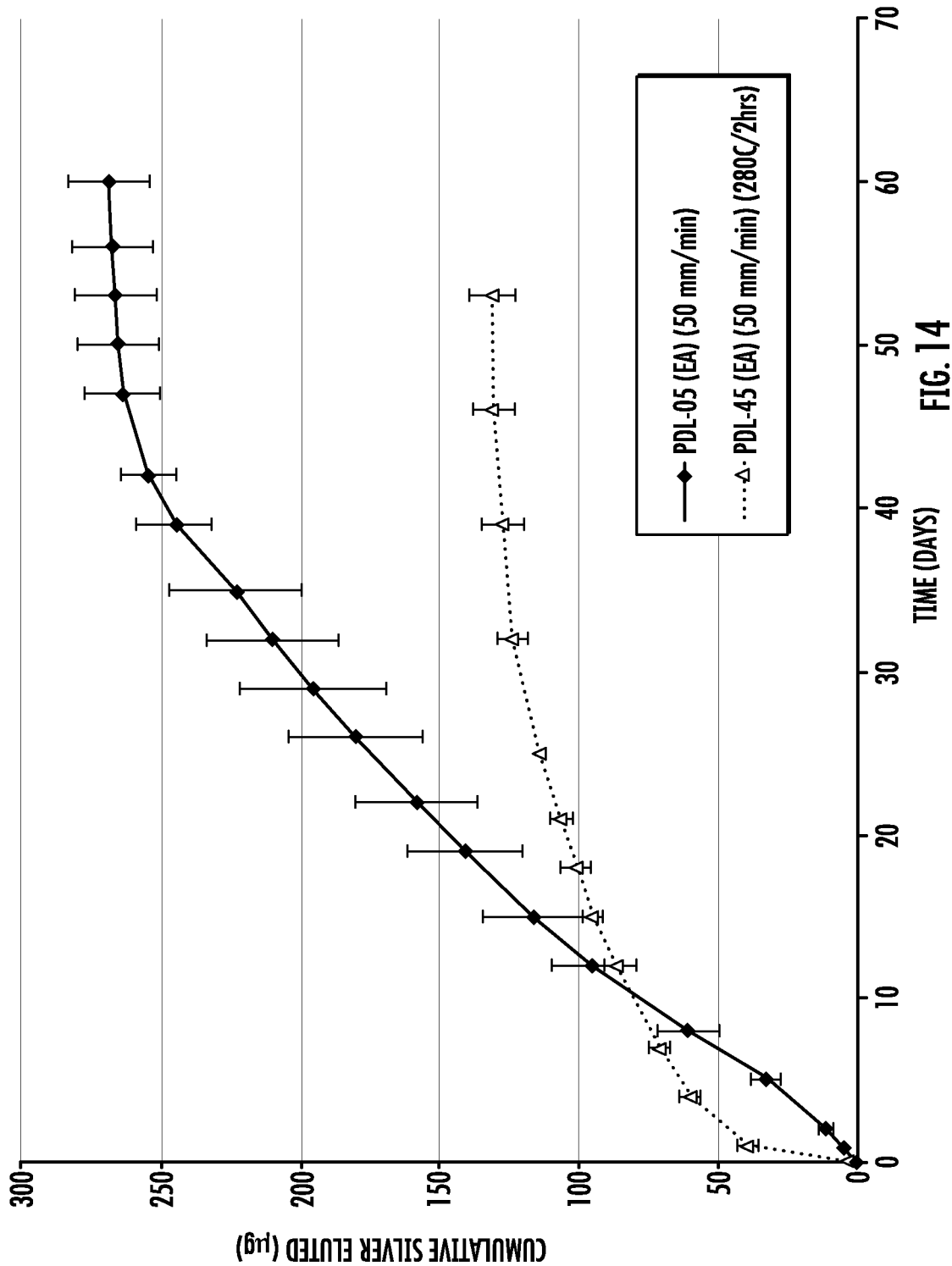
FIG. 14 shows a graph of experimental data relating to the rate of elution of silver ions from nails having polymeric coatings thereon.

In a further experiment, silver treated titanium parts prepared as described above in relation to the heat treatment studies carried out on the non-coated silver titanate test coupons were subject to a two (2) hour 280° C. heat treatment prior to polymer coating. The heat treatment had a significant effect on the in vitro elution kinetics, with only 39% of the silver eluted after 53 days compared to 79% for the non-heat-treated samples, as shown in FIG. 14. The slower elution rate associated with the heat-treated samples is believed to be due to a combination of microstructural changes in the titanate structure, combined with changes in the silver nano-particulate chemistry. Moreover, the heat-treated pins were photographed after elution and found to possess a uniform dark colour, thereby confirming that a significant quantity of the silver was retained within the titanate structure, as shown in FIG. 14.

Protection of the Polymer Coated Titanate from Abrasive Forces Using Design Features and/or Bushings The polymeric coating provides some level of lubricity to the implant during insertion into the bone canal. Equally, the thickness of the titanate and polymer coating layers may be minimized to approximately 1 and 3 µm respectively, which can help to reduce the risk of damage from mechanical abrasion during insertion via compression and torsional loading. Although these designs provide some level of protection to the antimicrobial coating during insertion into the bone canal or on the threaded portion of the implant during screw insertion, there is still a need for implementing further design features to mitigate this risk.

For example, as shown in FIGS. 15a and 15b, the use of polymeric bushings 102 to reduce metal on metal contact through screw holes 104 in the distal and proximal regions of the nail 106. In such a manner, the screw contacts the bushing, not the nail, thereby reducing the risk of abrasion of the antimicrobial coating.

Figure 16A:
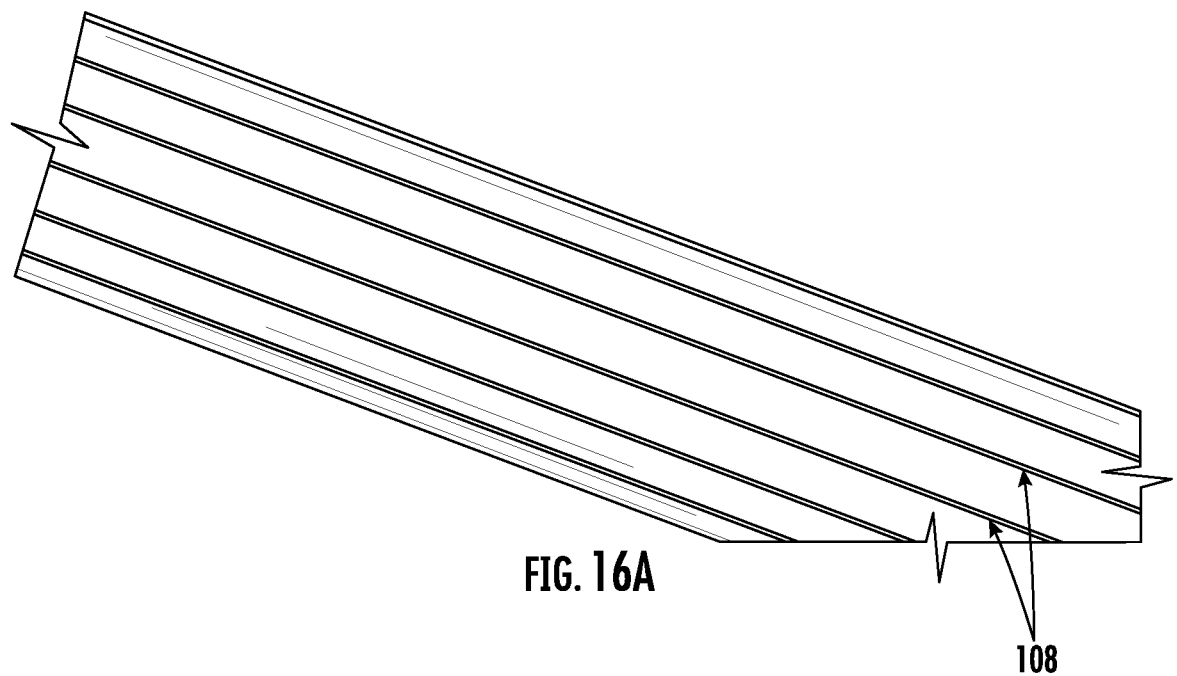
FIG. 16A shows a perspective view of a part of an orthopaedic implant having surface features thereon.
Figure 16B:
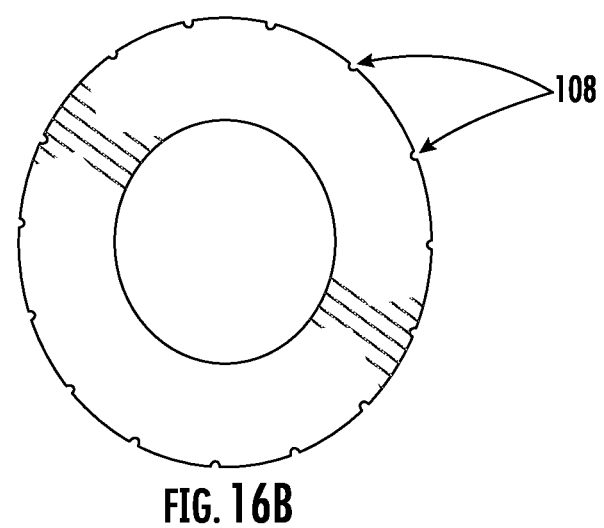

Alternatively, or additionally, the use of flutes or dovetails positioned along the length of the nail are also options for reducing the amount of contact points between the antimicrobial coating and the internal surfaces of the bone canal. An embodiment showing such features is shown in FIGS. 16a and 16b (the latter figure being a cross sectional view of the former), in which longitudinal channels 108 along the external surface of the nail are shown. Such surface features can be achieved using standard CNC machining processing or sculpture milling, for example.

Figure 17:
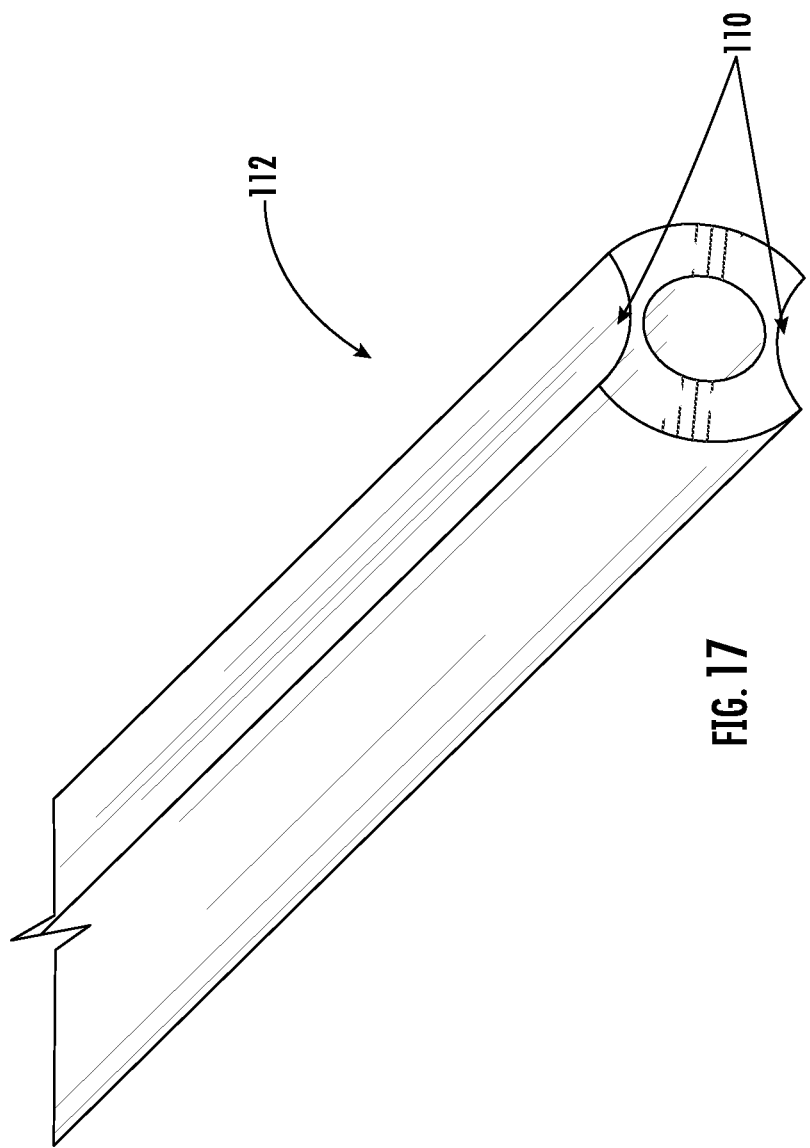
FIG. 17 shows a perspective view of an end of an orthopaedic implant having surface features thereon.
Figure 18:
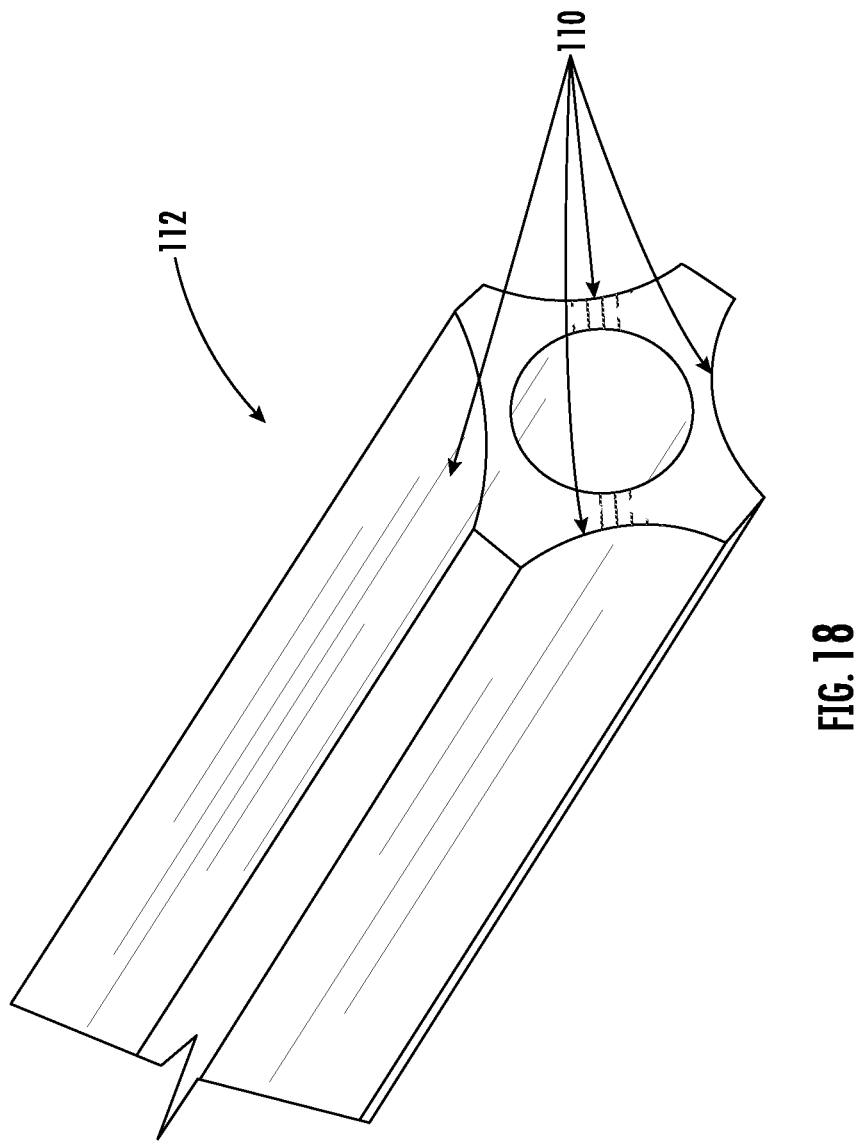
FIG. 18 shows a perspective view of an end of an orthopaedic implant having surface features thereon.

Alternatively, or additionally, the cross-sectional geometry of the nail can be altered from a circular to one which provides additional protection to two of the four surfaces during insertion into the bone canal by creating longitudinally extending recesses, which are offset from the internal surfaces of the bone canal. Example embodiments of this are show in FIG. 17 and FIG. 18 in which longitudinal recesses 110 (two and four respectively) extend along the length of the implant 112.

Attention is directed to all papers and documents which are filed concurrently herewith or previous to this specification in connection with this application and which are open to public inspection with this specification, and the contents of all such papers and documents are incorporated herein by reference in their entirety.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent, or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. An orthopaedic implant comprising:
a passivated titanium substrate;
silver deposited on the titanium substrate to form a silver titanate surface; and
a polymer coating on the silver titanate surface, wherein the polymer coating operable to elute the silver into a patient's body into which the orthopaedic implant is implanted for at least 14 consecutive days.

2. The orthopaedic implant of claim 1, wherein the polymer coating is operable to allow elution of silver into the body at a rate of at least 0.25 $\mu g/cm^2$ 24 $h^{-1}$, in use.

3. The orthopaedic implant of claim 1, wherein said substrate has silver deposited thereon at an amount of at least 10 $\mu g/cm^2$.

4. The orthopaedic implant of claim 1, wherein said passivated titanium substrate is obtainable by contacting the titanium substrate with a 7 to 13M solution of a group I or group II metal hydroxide to thereby passivate the titanium substrate, then contacting the passivated titanium substrate so obtained with silver.

5. The orthopaedic implant of claim 1, comprising at least one anchor point, configured for anchoring the orthopaedic implant in place in the body, in use.

6. The orthopaedic implant of claim 5, wherein the at least one anchor point comprises at least one bushing that protects the silver deposited on the at least one anchor point during anchoring of the orthopaedic implant.

7. The orthopaedic implant of claim 5, wherein the at least one anchor point comprises one or more surface features operable to reduce a size of a contact surface between the orthopaedic implant and an area within the body into which the orthopaedic implant is inserted, in use, wherein the one or more surface features comprises ribs, channels, or recesses.

8. The orthopaedic implant of claim 1, wherein the orthopaedic implant is in a form of a shoulder implant, a hip implant, a knee implant, a wrist implant, an interphalangeal implant, a partial or carpal joint implant, an ankle implant, an elbow implant, a spinal implant, an orthopaedic nail, a femoral nail, a tibial nail, an orthopaedic bone plate, a fastener, a screw, a wire, or a pin.

9. The orthopaedic implant of claim 1, wherein the silver titanate surface is treated with a blackening reducing agent, and wherein the silver is operable to be eluted at a rate of at least 0.25 $\mu g/cm^2$ 24 $h^{-1}$, for at least 14 consecutive days, in use.

10. The orthopaedic implant of claim 9, wherein the silver is in a form of silver nanoparticles.

11. The orthopaedic implant of claim 9, wherein the silver is in a form of silver ions.

12. The orthopaedic implant of claim 9, further comprising a polymer coating thereon, the polymer coating being applied to the titanium substrate having silver deposited thereon at a rate of between 10 mm/min and 1000 mm/min.

13. The orthopaedic implant of claim 12, wherein said polymer coating is applied to the titanium substrate having silver deposited thereon at a rate of between 10 mm/min and 1000 mm/min.

14. The orthopaedic implant of claim 9, wherein the blackening reducing agent comprises a sodium sulphide.

15. An orthopaedic implant comprising:
a titanium substrate;
silver, in a form of silver ions and/or silver nanoparticles, dispersed within the titanium substrate; and
a polymer coating deposited over the silver;
wherein the polymer coating is operable to elute the silver into a body into which the orthopaedic implant is implanted for at least 14 consecutive days; and
wherein the orthopaedic implant further comprises at least one anchor point configured for anchoring the orthopaedic implant in place in the body, in use, and the at least one anchor point comprises at least one bushing that protects the silver deposited on the at least one anchor point during anchoring of the orthopaedic implant.

16. The orthopaedic implant of claim 15, wherein the polymer coating is operable to allow elution of silver into the body at a rate of at least 0.25 $\mu g/cm^2$ 24 $h^{-1}$, in use.

17. The orthopaedic implant of claim 15, wherein the at least one anchor point comprises one or more surface features operable to reduce a size of a contact surface between the orthopaedic implant and an area within the body into which the orthopaedic implant is inserted, in use, wherein the one or more surface features comprises ribs, channels, or recesses.

18. The orthopaedic implant of claim 15, wherein the orthopaedic implant is in a form of a shoulder implant, a hip implant, a knee implant, a wrist implant, an interphalangeal implant, a partial or carpal joint implant, an ankle implant, an elbow implant, a spinal implant, an orthopaedic nail, a femoral nail, a tibial nail, an orthopaedic bone plate, a fastener, a screw, a wire, or a pin.

* * * * *